(12) United States Patent
Zargar et al.

(10) Patent No.: US 12,331,302 B2
(45) Date of Patent: Jun. 17, 2025

(54) FUNGAL AUTOINDUCIBLE EXPRESSION SYSTEM

(71) Applicants: Amin Zargar, Emeryville, CA (US); Jenny Landberg, Berkeley, CA (US); Jay D. Keasling, Berkeley, CA (US)

(72) Inventors: Amin Zargar, Emeryville, CA (US); Jenny Landberg, Berkeley, CA (US); Jay D. Keasling, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 959 days.

(21) Appl. No.: 17/092,031

(22) Filed: Nov. 6, 2020

(65) Prior Publication Data
US 2021/0139923 A1 May 13, 2021

Related U.S. Application Data

(60) Provisional application No. 62/933,191, filed on Nov. 8, 2019.

(51) Int. Cl.
*C12N 15/80* (2006.01)
*C12N 15/81* (2006.01)
*C12P 21/00* (2006.01)

(52) U.S. Cl.
CPC ............. *C12N 15/81* (2013.01); *C12P 21/00* (2013.01); *C12N 2800/102* (2013.01); *C12N 2830/002* (2013.01)

(58) Field of Classification Search
CPC .............. C12N 15/81; C12N 2800/102; C12N 2830/002; C12P 21/00
USPC ................................. 435/6.19, 7.2
See application file for complete search history.

(56) References Cited

U.S. PATENT DOCUMENTS

| | | |
|---|---|---|
| 4,500,707 A | 2/1985 | Caruthers et al. |
| 4,683,195 A | 7/1987 | Mullis et al. |
| 5,436,327 A | 7/1995 | Southern et al. |
| 5,602,034 A | 2/1997 | Takamp-Olson |
| 5,700,637 A | 12/1997 | Southern |

OTHER PUBLICATIONS

Davos et al., Proteins: Structure, Function and Genetics, 2000, vol. 41: 98-107.*
Wristlock et al., Quarterly Reviews of Biophysics 2003, vol. 36 (3): 307-340.*
Kwiatkowski et al., Biochemistry 38:11643-11650, 1999.*
Kisselev L., Structure, 2002, vol. 10: 8-9.*
Guo et al, Nature, 1997, 389, 40-46.*
Williams et al., "Engineered Quorum Sensing Using Pheromone-Mediated Cell-to-Cell Communication in *Saccharomyces cerevisiae*", ACS Synthetic Biology, 2:136-149 (2013).
Brockman et al., "Dynamic metabolic engineering: New strategies for developing responsive cell factories", Biotechnol. J. 10: 1360-1369 (2015).
Leavitt et al., "Coordinated transcription factor and promoter engineering to establish strong expression elements in *Saccharomyces cerevisiae*", Biotech. J 11:866-876 (2016).
Gibson et al., "Enzymatic assembly of DNA molecules up to several hundred kilobases." Nature Methods, 6:343-345 (2009).
Apel et al., "A Cas9-based toolkit to program gene expression in *Saccharomyces cerevisiae*", Nucleic Acids Research 45: 496-508 (2017).
Hubmann et al., "Natural and Modified Promoters for Tailored Metabolic Engineering of the Yeast *Saccharomyces cerevisiae*", Yeast Metabolic Engineering, 17-42 (2014).
Moon et al., "Enzymatic hydrolysis of food waste and ethanol fermentation", Int. J. Energy Research 33:164-172 (2009).
Martin et al., "Domestication of wild *Saccharomyces cerevisiae* is accompanied by changes in gene expression and colony morphology", Molecular Microbiology 47: 745-754 (2003).
Williams et al., "Quorum-sensing linked RNA interference for dynamic metabolic pathway control in *Saccharomyces cerevisiae*." Metabolic Engineering, 29, 124-134 (2015).
Zhang et al., "Conditional gene manipulation: Cre-ating a new biological era", J Zhejiang Univ Sci B., 13(7):511-524 (2012).
Neubauer et al., "Scale-down simulators for metabolic analysis of large-scale bioprocesses", Current Opinion in Biotechnology 21:114-121 (2010).

* cited by examiner

*Primary Examiner* — Robert B Mondesi
*Assistant Examiner* — Mohammad Y Meah
(74) *Attorney, Agent, or Firm* — Robin C. Chiang; LAWRENCE BERKELEY NATIONAL LABORATORY

(57) ABSTRACT

The present invention provides for a system comprising: (a) a first nucleic acid encoding an α-factor receptor operatively linked to a first promoter, (b) a second nucleic acid encoding a recombinase operatively linked to a promoter which is activated by an α-factor receptor bound to an α-factor, and (c) a third nucleic acid encoding a gene of interest (GOI) flanked by a pair of recombinase recognition sequences, recognized by the recombinase, operatively linked to a second promoter. The present invention provides for a genetically modified fungal cell comprising the system of the present invention.

21 Claims, 10 Drawing Sheets

FUNGAL AUTOINDUCIBLE EXPRESSION SYSTEM

CROSS-REFERENCE TO RELATED APPLICATIONS

This application claims priority to U.S. Provisional Patent Application Ser. No. 62/933,191, filed Nov. 8, 2019, which is hereby incorporated by reference.

STATEMENT OF GOVERNMENTAL SUPPORT

The invention was made with government support under Contract No. DE-AC02-05CH11231 awarded by the U.S. Department of Energy, and Grant No. F32GM125179 awarded by the National Institutes of Health. The government has certain rights in the invention.

FIELD OF THE INVENTION

The present invention is in the field of fungal gene expression.

BACKGROUND OF THE INVENTION

Inducible expression systems are especially valuable for producing compounds that are toxic for the production organism, or require allocation of resources such as cofactors and ATP. Although many pharmaceuticals and valuable chemicals are derived from pathways that have toxic intermediates, such as the mevalonate pathway, there is a lack of systems that allows for inducible expression without addition of an expensive compound or regulation of fermenter conditions.

In two previous studies, the α-factor-based mating response of Saccharomyces cerevisiae has been rewired to control protein and metabolite production in an autoinducible manner. In a publication by Williams et al. (Williams T. C, Nielsen, L. K., & Vickers, C. E. (2013). Engineered Quorum Sensing Using Pheromone-Mediated Cell-to-Cell Communication in Saccharomyces cerevisiae. ACS Synthetic Biology, 130107121842003) the α-factor producing gene MFα1 was put under control of the different promoters FUS1, FUS1J2 (both for a positive feedback loop) and ARO9 (inducible by aromatic amino acids). Expression of GFP was also controlled by the FUS1 promoter. Fluorescent output was measured for cells with the positive feedback loop and by induction with aromatic amino acids, with a maximum fold change of seven when comparing induced and not induced cultures. In this system, the gene expressing cell-cycle arrest protein Far1 was not deleted, as the authors could see that a deletion disrupts the α-factor sensing, and that a signaling response could not be sustained in a deletion strain. Therefore, cells did not grow to a higher OD than four, where after the α-factor concentration reached the threshold level that induces cell-cycle arrest. In a follow-up study, Williams et al. (Williams, T C, Averesch, N. J. H., Winter, G., Plan, M. R., Vickers, C. E., Nielsen, L. K., & Kromer, J. O. (2015). Quorum-sensing linked RNA interference for dynamic metabolic pathway control in Saccharomyces cerevisiae. Metabolic Engineering, 29, 124-134) engineered another system where production of para-hydroxybenzoic acid (PHBA) was induced by α-factor sensing. The ARO9 promoter controlled expression of α-factor, which when a certain threshold concentration had been reached, induced the FUS1J2 promoter through the Ste2-mediated MAPK signaling pathway. The FUS1J2 promoter controlled production of proteins involved in PHBA synthesis as well as expression of RNAis silencing nodes competing for resources with PHBA.

SUMMARY OF THE INVENTION

The present invention provides for a system comprising: (a) a first nucleic acid encoding an α-factor receptor operatively linked to a first promoter, (b) a second nucleic acid encoding a recombinase operatively linked to a promoter which is activated by an α-factor receptor bound to an α-factor (or alpha factor), and (c) a third nucleic acid encoding a gene of interest (GOI) flanked by a pair of recombinase recognition sequences, recognized by the recombinase, operatively linked to a second promoter.

In some embodiments, the α-factor receptor is STE2 and the first promoter is a native promoter of STE2. In some embodiments, the promoter which is activated by an α-factor receptor bound to an α-factor is a FUS1 promoter. In some embodiments, the first nucleic acid is stably integrated in a chromosome. In some embodiments, the second promoter is a constitutive promoter. In some embodiments, the first nucleic acid is stably integrated into a chromosome. In some embodiments, the second nucleic acid is an input plasmid. In some embodiments, the third nucleic acid is an output plasmid. In a particular embodiment, the system comprises the elements shown in FIG. 1D.

In some embodiments, the recombinase comprises a protein degradation tag. In some embodiments, the promoter which is activated by an α-factor receptor bound to an α-factor is a FUS1/2 promoter. In a particular embodiment, the system comprises the elements shown in FIG. 1E.

In some embodiments, the first promoter is a first inducible promoter. In some embodiments, the first nucleic acid further comprises a MFα1 gene operatively linked to a second inducible promoter, such as $P_{VAR*}$. In some embodiments, the nucleic acid encoding the α-factor receptor is operatively linked to $P_{STE2}$ and/or $P_{VAR*}$. In some embodiments, the second nucleic acid further comprises nucleic acid encoding BAR1 operatively linked to $P_{TETO3}$, and/or nucleic acid encoding rtTA* operatively linked to $P_{TDH3}$. In a particular embodiment, the system comprises the elements shown in FIG. 1F.

The present invention provides for a genetically modified fungal cell comprising the system of the present invention.

In some embodiments, the fungal cell is a yeast cell. In some embodiments, the yeast cell is a Saccharomyces cell. In some embodiments, the Saccharomyces cell is a Saccharomyces cerevisiae cell. In some embodiments, the Saccharomyces cerevisiae cell is a cell of the Saccharomyces cerevisiae BY4741 strain.

In some embodiments, the system comprises a yeast mating signaling pathway for inducing expression of a gene of interest, or a plurality of gene of interest. The response is induced by α-factor binding to the STE2 receptor, which activates the FUS1 promoter through a MAPK-mediated response pathway. The FUS1 promoter controls a recombinase (such as a Cre recombinase) that, when expressed, performs a recombination-based removal of a STOP codon, enabling expression of the gene(s) of interest (GOI) cloned after the STOP codon.

A benefit of the system is the permanent DNA change, thereby reducing, or eliminating, the potential of mutations that would "break" the circuit. The gene transitions from the "OFF" to the "ON" state via this cell density dependent genetic circuit.

In some embodiments, the system comprises a reporter gene (such as a fluorescent reporter gene, such as the gene encoding a GFP) as the GOI, and/or an additional or heterologous α-factor gene externally which is capable of expressing α-factor (FIG. 1D). In some embodiments, there is no endogenous production of α-factor as the MFα1 gene is not yet integrated in the strain. In this experiment, we could see that expression of the fluorescent reporter gene was induced before α-factor was added. This is due to high basal level expression of Cre recombinase from the FUS1 promoter. In some embodiments, the FUS1 promoter is changed to a version with lower basal level expression (PFUS1J2), and introduced a ubiM degradation tag on the Cre recombinase (FIG. 1E). This improves the system significantly. In some embodiments, the protein production level is equal to or more than about 2-fold lower compared to those that can be achieved with commonly used constitutive promoters.

In some embodiments, one or more nucleic acid is stably integrated in a fungal genome or chromosome. In some embodiments, one or more nucleic acid is on a vector or expression vector. In some embodiments, one or more nucleic acid is heterologous to the fungal cell. In some embodiments, the GOI is heterologous to the fungal cell. In some embodiments, one or more promoters is heterologous to the fungal cell, the GOI. In some embodiments, one or more of the genes encodes for a functional fragment of the wild-type of the gene.

The present invention provides for a method comprising: (a) providing a system or a genetically modified fungal cell comprising the system of the present invention, (b) introducing or expressing an α-factor to the system, and (c) expressing the GOI.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1A:
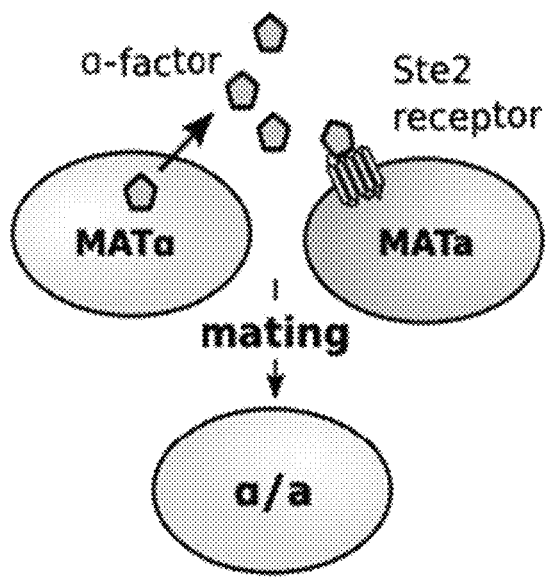
FIG. 1A shows a mating signaling in yeast.

Before the invention is described in detail, it is to be understood that, unless otherwise indicated, this invention is not limited to particular sequences, expression vectors, enzymes, yeast microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to a "vector" includes a single vector as well as a plurality of vectors, either the same (e.g., the same operon) or different; reference to "cell" includes a single cell as well as a plurality of cells; and the like.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" refers to a value including 10% more than the stated value and 10% less than the stated value.

The term "heterologous DNA" as used herein refers to a polymer of nucleic acids wherein at least one of the following is true: (a) the sequence of nucleic acids is foreign to (i.e., not naturally found in) a given yeast microorganism; (b) the sequence may be naturally found in a given yeast microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a yeast microorganism, wherein the expression vector contains a nucleic acid sequence coding for an enzyme that is not normally found in a yeast microorganism. With reference to the yeast microorganism's genome, then, the nucleic acid sequence that codes for the enzyme is heterologous.

The terms "expression vector" or "vector" refer to a compound and/or composition that transduces, transforms, or infects a yeast microorganism, thereby causing the cell to express nucleic acids and/or proteins other than those native to the cell, or in a manner not native to the cell. An "expression vector" contains a sequence of nucleic acids (ordinarily RNA or DNA) to be expressed by the yeast microorganism. Optionally, the expression vector also comprises materials to aid in achieving entry of the nucleic acid into the yeast microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a yeast microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a yeast microorganism or cell. Only when the sequence of nucleic acids becomes stably replicated by the cell does the yeast microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a yeast microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state or free of components from a yeast cell or culture medium from which the material is obtained.

The term "operably linked" refers to a functional linkage between a nucleic acid expression control sequence (such as a promoter) and a second nucleic acid sequence, wherein the expression control sequence directs transcription of the nucleic acid corresponding to the second sequence.

The term "functional fragment" refers to an enzyme that has an amino acid sequence that is at least 70%, 75%, 80%, 85%, 90%, 95% or 99% identical to the amino acid sequence of any one of the proteins or enzymes described in this specification or in an incorporated reference. The functional fragment retains amino acids residues that are recognized as conserved for the biological activity of the protein or enzyme. The functional fragment may have non-conserved amino acid residues replaced or found to be of a different amino acid, or amino acid(s) inserted or deleted, but which does not affect or has insignificant effect on the biological activity of the functional fragment. The functional fragment has a biological activity that is identical or essentially identical to the enzymatic activity any one of the enzymes described in this specification or in an incorporated reference. The functional fragment may be found in nature or be an engineered mutant thereof. The mutant may have one or more amino acids substituted, deleted or inserted, or a combination thereof, as compared to the protein or enzyme described in this specification or in an incorporated reference.

The term "yeast" refers to any yeast species including: ascosporogenous yeasts (Endomycetales), basidiosporogenous yeasts and yeast belonging to the Fungi imperfecti (Blastomycetes). The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium* and *Filobasidiella*. Yeast belonging to the Fungi Imperfecti are divided into two families, Sporobolomycetaceae (e.g., genera *Sporobolomyces, Bullera*) and Cryptococcaceae (e.g., genus *Candida*). Of particular interest to the present invention are species within the genera *Pichia, Kluyveromyces, Saccharomyces, Schizosaccharomyces* and *Candida*. Of particular interest are the *Saccharomyces* species *S. cerevisiae, S. carlsbergensis, S. diastaticus, S. douglasii, S. kluyveri, S. norbensis* and *S. oviformis*. Species of particular interest in the genus *Kluyveromyces* include *K. lactis*. Since the classification of yeast may change in the future, for the purposes of this invention, yeast shall be defined as described in Biology and Activities of Yeast (F. A. Skinner, S. M. Passmore & R. R. Davenport eds. 1980) (Soc. App. Bacteriol. Symp. Series No. 9). In addition to the foregoing, those of ordinary skill in the art are presumably familiar with the biology of yeast and the manipulation of yeast genetics. See, e.g., Biochemistry and Genetics of Yeast (M. Bacila, B. L. Horecker & A. O. M. Stoppani eds. 1978); The Yeasts (A. H. Rose & J. S. Harrison eds., 2nd ed., 1987); The Molecular Biology of the Yeast Saccharomyces (Strathern et al. eds.

The transition from the "OFF" to "ON" state can be tuned by manipulating the circuit. The α-factor can be produced by the yeast itself, from the MFα1 gene, which is integrated in the genome. The Ste2 receptor protein can be expressed from the genome-integrated STE2 gene. By varying the expression strength, i.e., the strength of the promoter controlling MFα1 and STE2, transcription of the recombinase, such as Cre recombinase, from the FUS1 promoter can be initiated at different time points and cell densities. Using strong promoters controlling MFα1 and STE2, expression of the gene of interest can be induced at an earlier time point and optical density (OD), and vice versa. a factor signaling is naturally used by yeast to induce cell mating. In some embodiments, the strains are deleted for FAR1 and FUS1 to prevent the yeast mating response. In some embodiments, the native gene encoding the a factor-degrading protease Bar1 is deleted. In some embodiments, the genes encoding MFα1 and STE2 are introduced into the genome, under the control of promoters PTDH3, PPGK1, PYEF3 and/or PACT1, which should provide a suite of OD-dependent activations.

A major issue with this system is potential premature activation. During the cloning and preculture phase, premature activation could result in a system that is already "ON". This is prevented b means of a second genetic circuit. In some embodiments, the genes responsible for producing and responding to the α-factor are constitutive, they are produced during cloning and pre-culturing. To prevent induction during these steps, the gene encoding Bar1 is placed under control of a tetracycline-inducible promoter. This promoter is induced by the reverse tetracycline transactivator (rtTA) when rtTA binds doxycycline. Addition of doxycycline can be used as a control mechanism, as it leads to expression of Bar1, which degrades α-factor and prevents induction of the system during cloning, transformation and pre-culturing (FIG. 1F).

The α-factor mating response has previously been rewired for protein and metabolite production. In Williams et al. (2013), MFα1 was put under control of the different promoters FUS1, FUS1J2 (both for a positive feedback loop) and ARO9 (inducible by aromatic amino acids). Expression of GFP was controlled by the FUS1 promoter. Fluorescent output was measured for cells with the positive feedback loop and by induction with aromatic amino acids, with a maximum fold change of 7 when comparing induced and not induced cultures. In this system, FAR1 was not deleted, as the authors could see that it disrupted the α-factor sensing and that a signaling response could not be sustained in a deletion strain. Therefore, cells did not grow to a higher OD than 4, where after the α-factor concentration reached the threshold level that induces cell-cycle arrest.

Williams et al. (2015) reports engineering another system where production of para-hydroxybenzoic acid (PHBA) was induced by α-factor sensing. The ARO9 promoter controlled expression of α-factor, which, when a certain threshold concentration had been reached, induced the FUS1J2 promoter through the Ste2-mediated MAPK signaling pathway. The FUS1J2 promoter controlled production of proteins involved in PHBA synthesis as well as expression of RNAis silencing nodes competing for resources with PHBA.

The major differentiation between these systems and ours is the recombinase enabling tunable levels of expression. These systems rely on the pFus promoter to activate expression. This limits autonomous activation to a single weak promoter (pFus), and more importantly, requires that the FAR1 gene remain expressed. As the FAR1 gene causes cell cycle arrest, these systems contain much lower levels of growth accumulation.

The Cre recombinase is a tyrosine recombinase commonly used to generate knockouts and conditional knockouts. An inducible version of this system is used in eukaryotes to generate knockouts to study embryonic development through the addition of tetracycline and tamoxifen (Zhang et al. 2012). However, this has never been yet shown to be used for a metabolic pathway in eukaryotes.

In some embodiments, the recombinase comprises the amino acid sequence of a recombinase listed in Table 1. Recombinases useful for this invention include, but are not limited to, to the recombinases listed in Table 1.

TABLE 1

Recombinases.

| # | Name | Host | Organism | Gene | Accession |
|---|------|------|----------|------|-----------|
| 1 | BSu_xerC | Bacillus subtilis | chromosome | codV | P39776 |
| 2 | BSu_xerD | Bacillus subtilis | chromosome | ripX | P46352 |
| 3 | BSu_ydcL | Bacillus subtilis | chromosome | ydcL | A69774 |
| 4 | CBu_tnpA | Clostridium butyricum | chromosome | tnpA | S40097 |
| 5 | ColID | Escherichia coli | plasmid F | D | P06615 |
| 6 | CP4-57 | Escherichia coli | chromosome | Int | P32053 |
| 7 | Cre | Escherichia coli | phage P1 | Int | P06956 |
| 8 | D29 | Mycobacterium smegmatis | phage D29 | Int | AAC18476 |
| 9 | DLP12 | Escherichia coli | phage DLP12 | Int | P24218 |
| 10 | DNo_int | Dichelobacter nodosus | chromosome | Orf | AAB00935 |
| 11 | ECo_fimB | Escherichia coli | chromosome | fimB | P04742 |
| 12 | ECo_fimE | Escherichia coli | chromosome | fimE | P04741 |
| 13 | ECo_orf | Escherichia coli | chromosome | b2442 | A65019 |
| 14 | ECo_xerC | Escherichia coli | chromosome | xerC | C37841 |
| 15 | ECo_xerD | Escherichia coli | chromosome | xerD | P21891 |
| 16 | HIn_orf | Haemophilus influenzae | chromosome | orf1572 | P46495 |
| 17 | HIn_rci | Haemophilus influenzae | chromosome | rci | P45198 |
| 18 | HIn_xerC | Haemophilus influenzae | chromosome | xerC | P44818 |
| 19 | HIn_xerD | Haemophilus influenzae | chromosome | xerD | P44630 |

TABLE 1-continued

Recombinases.

| # | Name | Host | Organism | Gene | Accession |
|---|------|------|----------|------|-----------|
| 20 | HK22 | *Escherichia coli* | phage HK022 | int | AAF30377 |
| 21 | HP1 | *Haemophilus influenzae* | phage HP1 | int | P21442 |
| 22 | L2 | *Acholeplasma* sp. | phage L2 | int | AAA87961 |
| 23 | L5 | *Mycobacterium tuberculosis* | phage L5 | int | CAA79409 |
| 24 | L54 | *Staphylococcus aureus* | phage L54 | int | P20709 |
| 25 | Lambda | *Escherichia coli* | phage lambda | int | AAA96562 |
| 26 | LLe_orf | *Lactobacillus leichmannii* | chromosome | orf | CAA55635 |
| 27 | LLe_xerC | *Lactobacillus leichmannii* | chromosome | xerC | CAA59018 |
| 28 | phi10MC | *Oenococcus oeni* | phage phi10MC | int | AAD00268 |
| 29 | MJa_orf | *Methanococcus jannaschi* | chromosome | orf | Q57813 |
| 30 | MLe_xerD | *Mycobacterium leprae* | chromosome | xerD | S72959 |
| 31 | MPa_int | *Mycobacterium paratuberculosis* | chromosome | int | AAA88834 |
| 32 | MTu_int | *Mycobacterium tuberculosis* | chromosome | int | B70965 |
| 33 | MTu_xerC | *Mycobacterium tuberculosis* | chromosome | xerC | Q10815 |
| 34 | MV4 | *Lactobacillus delbrueckii* | phage MV4 | int | AAC48859 |
| 35 | MX8 | *Myxococcus xanthus* | phage Mx8 | int | AAC48895 |
| 36 | pAE1 | *Alcaligenes eutrophus* | plasmid pAE1 | orf | AAA87238 |
| 37 | pCL1 | *Chlorobium limicola* | plasmid pCL1 | fim | AAB36935 |
| 38 | pDU1 | *Nostoc* sp. | plasmid pDU1 | orf | AAA17517 |
| 39 | pMEA | *Amycolatopsis methanolica* | plasmid pMEA300 | orf | AAB00469 |
| 40 | RSp_EF | *Rhizobium* sp. | plasmid pNG234a | EF | P55429 |
| 41 | RSp_GC | *Rhizobium* sp. | plasmid pNG234a | GC | P55459 |
| 42 | RSp_QK | *Rhizobium* sp. | plasmid pNG234a | QK | P55632 |
| 43 | RSp_RA | *Rhizobium* sp. | plasmid pNG234a | RA | AAB92467 |
| 44 | RSp_RB | *Rhizobium* sp. | plasmid pNG234a | RB | P55635 |
| 45 | RSp_RC | *Rhizobium* sp. | plasmid pNG234a | RC | P55636 |
| 46 | RSp_RD | *Rhizobium* sp. | plasmid pNG234a | RD | P55637 |
| 47 | RSp_RE | *Rhizobium* sp. | plasmid pNG234a | RE | P55638 |
| 48 | RSp_RF | *Rhizobium* sp. | plasmid pNG234a | RF | P55639 |
| 49 | pSAM2 | *Streptomyces ambofaciens* | plasmid pSAM2 | orf | P15435 |
| 50 | pSDL2 | *Salmonella dublin* | plasmid pSDL2 | resV | A38114 |
| 51 | pSE101 | *Saccharopolyspora erythraea* | plasmid pSE101 | orf | S41725 |
| 52 | pSE211 | *Saccharopolyspora erythraea* | plasmid pSE211 | orf | P22877 |
| 53 | pWS58 | *Lactobacillus delbrueckii* | plasmid pWS58 | orf | CAA90472 |
| 54 | phi-11 | *Staphylococcus aureus* | phage phi11 | int | AAA32198 |
| 55 | phi-13 | *Staphylococcus aureus* | phage phi13 | int | S52761 |
| 56 | phi-80 | *Escherichia coli* phage | phage phi80 | int | CAA27683 |
| 57 | phi-adh | *Lactobacillus gasseri* | phage phi-adh | int | JN0535 |
| 58 | phi-CTX | *Pseudomonas aeruginosa* | phage phiCTX | int | CAA74224 |
| 59 | phi-g1e | *Lactobacillus* sp. | phage phi-g1e | int | T13182 |
| 60 | phi-LC3 | *Lactococcus lactis* | phage phiLC3 | int | A47085 |
| 61 | phi-R73 | *Escherichia coli* | phage phi-R73 | int | A42465 |
| 62 | P186 | *Escherichia coli* | phage 186 | int | AAC34175 |
| 63 | P2 | *Escherichia coli* | phage P2 | int | AAD03297 |
| 64 | P21 | *Escherichia coli* | phage P21 | int | AAC48886 |
| 65 | P22 | *Salmonella typhimurium* | phage P22 | int | AAF75002 |
| 66 | P4 | *Escherichia coli* | phage P4 | int | CAA29379 |
| 67 | P434 | *Escherichia coli* | phage 434 | int | P27078 |
| 68 | PAe_xerC | *Pseudomonas aeruginosa* | chromosome | sss | AAG08665 |
| 69 | PMi_fimB | *Proteus mirabilis* | chromosome | fimB | CAB61438 |
| 70 | R721 | *Escherichia coli* | plasmid IncI2 (R721) | rcb | G45252 |
| 71 | Rci | *Escherichia coli* | plasmid IncI1 (R64) | rci | P10487 |
| 72 | SF6 | *Shigella flexneri* | phage Sf6 | int | P37317 |
| 73 | SLP1 | *Streptomyces coelicolor* | plasmid SLP1 | orf | CAC08268 |
| 74 | IntI3 | *Serratia marcescens* | chromosome | orf | BAA08929 |
| 75 | SsrA | *Methanosarcina acetivorans* | plasmid pC2A | ssrA | AAB39744 |
| 76 | SSV1 | *Sulfolobus* sp. | phage SSV1 | int | CAA30211 |
| 77 | T12 | *Streptococcus pyogenes* | phage T12 | int | AAC488867 |
| 78 | IntI1 | *Escherichia coli* | transposon Tn21 | int | AAA82254 |
| 79 | Tn4430 | *Bacillus thuringiensis* | transposon Tn4430 | int | CAA30491 |
| 80 | Tn5041 | *Pseudomonas* sp. | transposon Tn5041 | orf1 | CAA67462 |
| 81 | Tn5252 | *Streptococcus pneumoniae* | transposon Tn5252 | int | A55863 |
| 82 | Tn5276 | *Lactobacillus lactis* | transposon Tn5276 | int | C55205 |
| 83 | Tn554a | *Staphylococcus aureus* | transposon Tn554 | tnpA | P06696 |
| 84 | Tn554b | *Staphylococcus aureus* | transposon Tn554 | tnpB | P06697 |
| 85 | IntI2 | *Escherichia coli* | transposon Tn7 | int | CAA05031 |
| 86 | Tn916 | *Entercoccus faecalis* | transposon Tn916 | int | P22886 |

TABLE 1-continued

Recombinases.

| # | Name | Host | Organism | Gene | Accession |
|---|---|---|---|---|---|
| 87 | Tuc | *Lactobacillus lactis* | phage Tuc2009 | int | AAA32608 |
| 88 | BZo_int | *Bergeyella zoohelcum* | chromosome | orf | AAA50502 |
| 89 | ASp_xisA | *Anabaena* sp. | chromosome | xisA | P08862 |
| 90 | ASp_xisC | *Anabaena* sp. | chromosome | xisC | Q44217 |
| 91 | FLP | *Saccharomyces cerevisiae* | plasmid 2μ | FLP | J01347 |
| 92 | pKD1 | *Kluyveromyces lactis* | plasmid pKD1 | FLP | P13783 |
| 93 | pSB2 | *Zygosaccharomyces bailii* | plasmid pSB2 | FLP | M18274 |
| 94 | pSB3 | *Zygosaccharomyces bisporus* | plasmid pSB3 | FLP | P13784 |
| 95 | pSM1 | *Zygosaccharomyces fermentati* | plasmid pSM1 | FLP | P13770 |
| 96 | pSR1 | *Zygosaccharomyces rouxii* | plasmid pSR1 | FLP | P13785 |
| 97 | HPy_xerC | *Helicobacter pylori* | chromosome | xerC | C64604 |
| 98 | HPy_xerD | *Helicobacter pylori* | chromosome | xerD | C64644 |
| 99 | Eco_Rac | *Escherichia coli* | chromosome | int | P76056 |
| 100 | Eco_Qin | *Escherichia coli* | chromosome | int | P76168 |
| 101 | CP4-6 | *Escherichia coli* | chromosome | orf | P71928 |
| 102 | E14 | *Escherichia coli* | chromosome | int | P75969 |
| 103 | MGo_orf | *Mycobacterium gordonae* | chromosome | orf | AAB54012 |
| 104 | MLe_xerC | *Mycobacterium leprae* | chromosome | xerC | CAB10656 |
| 105 | MTu_xerD | *Mycobacterium tuberculosis* | chromosome | xerD | CAB10958 |
| 106 | pEAF | *Escherichia coli* | plasmid EAF | rsv | AAC44039 |
| 107 | PFl_xerC | *Pseudomonas fluorescens* | chromosome | sss | T10461 |
| 108 | PWi_orf | *Protothera wickerhamii* | mitochondria | ymf42 | T11912 |
| 109 | Sfi21 | *Streptococcus thermophilus* | phage Sfi21 | int | AAD44095 |
| 110 | phi-r1t | *Lactobacillus lactis* | phage r1t | int | AAB18676 |
| 111 | STy_xerC | *Salmonella typhimurium* | chromosome | xerC | P55888 |
| 112 | STy_xerD | *Salmonella typhimurium* | chromosome | xerD | P55889 |
| 113 | SSp_orf | *Synechocystis* sp. | chromosome | orf | BAA16682 |
| 114 | DNo_orf | *Dichelobacter nodosus* | chromosome | orf | AAB00935 |
| 115 | VCh_orf | *Vibrio cholerae* | chromosome | orf | AAC44230 |
| 116 | MMa_xerC | *Methanothermobacter marburgensis* | chromosome | xerC | D69219 |
| 117 | ECo_orf2 | *Escherichia coli* | chromosome | intB | P39347 |
| 118 | SIn_orf | *Salmonella infantis* | chromosome | orf | J03391 |
| 119 | BK-T | *Lactococcus lactis* | phage BK-T | int | T13262 |
| 120 | phi-42 | *Staphylococcus aureus* | phage phi42 | int | AAA91615 |
| 121 | FRAT1 | *Mycobacterium* sp. | phage FRAT1 | int | P25426 |
| 122 | HZe_vlf1 | *Helicoverpa zea* | chromosome | vlf1 | AAA58702 |
| 123 | pKW1 | *Kluveromyces waltii* | plasmid pKW1 | FLP | X56553 |
| 124 | CBu_tnpB | *Clostridium butyricum* | chromosome | tnpB | S40098 |
| 125 | S2 | *Haemophilus influenzae* | phage S2 | int | CAA96221 |
| 126 | NBU1 | *Bacteroides uniformis* | plasmid NBU1 | int | AAF74437 |
| 127 | Tn1545 | *Streptococcus pneumoniae* | transposon Tn1545 | int | P27451 |
| 128 | T270 | *Streptococcus pyogenes* | phage T270 | int | AAA85500 |
| 129 | PMi_xerC | *Proteus mirabilis* | chromosome | xerC | AAB 87500 |
| 130 | PMi_xerD | *Proteus mirabilis* | chromosome | xerD | AAB 87499 |
| 131 | phiV | *Shigella flexneri* | phage V | int | AAB72135 |
| 132 | O1205 | *Streptococcus thermophilus* | phage 01205 | int | T13289 |
| 133 | Tn4556 | *Streptomyces fradiae* | transposon Tn4556 | int | P20184 |
| 134 | MS6 | *Mycobacterium* sp. | phage Ms6 | int | AAD03774 |
| 135 | pFAJ | *Rhodococcus erythropolis* | plasmid pFAJ2600 | pmrA | AAC45806 |
| 136 | SMa_xerC | *Serratia marcescens* | chromosome | xerC | AAC46276 |
| 137 | pTiA6 | *Agrobacterium tumefaciens* | plasmid pTiA6NC | int | AAB91569 |
| 138 | AAe_orf | *Aquifex aeolicus* | chromosome | int | G70397 |
| 139 | Tn557 | *Staphylococcus aureus* | transposon Tn557 | int | AAC28969 |
| 140 | EAe_int | *Enterobacter aerogenes* | chromosome | int | AAB95339 |
| 141 | SF2 | *Shigella flexneri* | phage Sf2 | int | AAC39270 |
| 142 | ECo_yfdB | *Escherichia coli* | chromosome | yfdB | P37326 |
| 143 | RP3 | *Streptomyces rimosus* | phage RP3 | int | X80661 |
| 144 | VWB | *Streptomyces venezuelae* | phage VWB | int | CAA03882 |
| 145 | SEx_vlf1 | *Spodoptera exigua* | chromosome | vlf1 | AAF33611 |
| 146 | STy_rci | *Salmonella typhimurium* | chromosome | rci | AAC38070 |
| 147 | PPu_orf | *Pseudomonas putida* | chromosome | orf | CAA06238 |
| 148 | A2 | *Lactobacillus casei* | phage A2 | int | CAA73344 |
| 149 | pECE1 | *Aquifex aeolicus* | plasmid ece1 | int | AAC07955 |
| 150 | MLo_int | *Mesorhizobium loti* | chromosome | intS | AAC24508 |
| 151 | SRu_orf | *Selenomonas ruminantium* | chromosome | orf | BAA24921 |
| 152 | pQPRS | *Coxiella burnetti* | plasmid pQPRS | int | CAA75853 |
| 153 | PRe_orf | *Panagrellus redivivus* | chromosome | orf | CAA43185 |
| 154 | CEl_orf | *Caenorhabditis elegans* | chromosome | orf | Z82079 |
| 155 | IntI4 | *Vibrio cholerae* | chromosome | intI4 | AAF71178 |
| 156 | SMu_orf | *Streptococcus mutans* NG8 | chromosome | orfA | AAC17173 |

TABLE 1-continued

Recombinases.

| # | Name | Host | Organism | Gene | Accession |
|---|---|---|---|---|---|
| 157 | phiU | Rhizobium leguminosarum | phage phiU | int | BAA25885 |
| 158 | PHo_xerC | Pyrococcus horikoshii | chromosome | xerC | B71194 |
| 159 | RCa_orf1 | Rhodobacter capsulatus | chromosome | orf1 | T03499 |
| 160 | RCa_orf2 | Rhodobacter capsulatus | chromosome | orf2 | T03567 |
| 161 | Tn5382 | Enterococcus faecium | transposon Tn5382 | int | AAC34799 |
| 162 | psiM2 | Methanothermobacter marburgensis | phage PsiM2 | int | T12745 |
| 163 | STy_orf | Salmonella typhimurium | chromosome | orf | T03001 |
| 164 | MTu_orf | Mycobacterium tuberculosis | chromosome | Rv2659c | G70966 |
| 165 | TPa_xerC | Treponema pallidum | chromosome | codV | AAC65375 |
| 166 | TPa_xerD | Treponema pallidum | chromosome | xprB | AAC65379 |
| 167 | CTr_xerC | Chlamydia trachomatis | chromosome | xerC | AAC67942 |
| 168 | CTr_xerD | Chlamydia trachomatis | chromosome | xerD | AAC68462 |
| 169 | phiPVL | Staphylococcus aureus | phage phiPVL | int | BAA31902 |
| 170 | pNL1 | Sphingomonas aromaticivorans | plasmid pNL1 | int | AAD03886 |
| 171 | CP4-157 | Escherichia coli O157:H7 | chromosome | int | AAC31482 |
| 172 | SAu_xerD | Staphylococcus aureus | chromosome | xerD | AAC64162 |
| 173 | YPe_orf | Yersinia pestis | chromosome | orf | AAC69581 |
| 174 | RPr_xerD | Rickettsia prowazekii | chromosome | xerD | B71693 |
| 175 | RPr_xerC | Rickettsia prowazekii | chromosome | xerC | B71643 |
| 176 | VCh_SXT | Vibrio cholerae | chromosome | orf | AAF93686 |
| 177 | AAc_orf | Actinob. actinomycetemcomitans | chromosome | orf | AAC70901 |
| 178 | MAV1 | Mycoplasma arthritidis | chromosome | int | AAC33780 |
| 179 | fOg44 | Oenococcus oeni | phage fOg44 | int | AAD10711 |
| 180 | SFX | Shigella flexneri | phage SFX | int | AAD10295 |
| 181 | Tn4371 | Ralstonia eutropha | transposon Tn4371 | int | CAA71790 |
| 182 | HPy_orf | Helicobacter pylori | chromosome | orf | A71869 |
| 183 | CPn_xerC | Chlamydia pneumoniae | chromosome | xerD | BAA99231 |
| 184 | CPn_xerD | Chlamydia pneumoniae | chromosome | xerC | BAA98236 |
| 185 | K139 | Vibrio cholerae | phage K139 | int | AAD22068 |
| 186 | PPu_orf2 | Pseudomonas putida | chromosome | orf | BAA75916 |
| 187 | pPZG | Pantoea citrea | plasmid pPZG500 | int | AAD21210 |
| 188 | H19J | Escherichia coli | phage H19J | int | CAB38715 |
| 189 | phi304L | Corynebacterium glutamicum | phage phi304L | int | CAB38562 |
| 190 | SCo_orf | Streptomyces coelicolor | chromosome | orf | T36198 |
| 191 | phi16 | Corynebacterium glutamicum | phage phi16 | int | CAA73074 |
| 192 | BHa_xerC | Bacillus halodurans | chromosome | codV | BAB06184 |
| 193 | XFa_xerC | Xylella fastidiosa | chromosome | xerC | AAF84292 |
| 194 | BHa_xerD | Bacillus halodurans | chromosome | xerD | BAB05248 |
| 195 | PAe_xerD | Pseudomonas aeruginosa | chromosome | xerD | AAG07125 |
| 196 | VCh_xerC | Vibrio cholerae | chromosome | xerC | AAF93305 |
| 197 | VCh_xerD | Vibrio cholerae | chromosome | xerD | AAF95562 |
| 198 | NMa_xerC | Neisseria meningitidis ser. A | chromosome | xerC | CAB83879 |
| 199 | NMb_xerC | Neisseria meningitidis ser. B | chromosome | xerC | AAF42202 |
| 200 | XFa_xerD | Xylella fastidiosa | chromosome | xerD | AAF84234 |
| 201 | CMu_xerC | Chlamydia muridarum | chromosome | xerC | AAF73578 |
| 202 | SAu_xerC | Staphylococcus aureus | chromosome | xerC | AAF89877 |
| 203 | NMa_xerD | Neisseria meningitidis ser. B | chromosome | xerD | AAF41164 |
| 204 | NMb_xerD | Neisseria meningitidis ser. A | chromosome | xerD | CAB84234 |
| 205 | CMu_xerD | Chlamydia muridarum | chromosome | xerD | AAF39124 |
| 206 | PAb_xerD | Pyrococcus abysii | chromosome | xerD | A75153 |
| 207 | pI3 | Deinococcus radiodurans | plasmid pI3 | ResU | AAF44051 |
| 208 | pTiSAK | Agrobacterium tumefaciens | plasmid TiSAKURA | orf36 | BAA87661 |
| 209 | HPj_xerC | Helicobacter pylori J | chromosome | xerC | B71910 |
| 210 | TMa_xerC | Thermotoga maritima | chromosome | xerC | D72312 |
| 211 | CJe_xerD | Campylobacter jejuni | chromosome | xerD | CAB73128 |
| 212 | APe_xerD | Aeropyrum pernix | chromosome | xerD | G72672 |
| 213 | PSy_orf | Pseudomonas syringae | chromosome | orfF | CAB96970 |
| 214 | MM1 | Streptococcus pneumoniae | phage MM1 | int | CAB96616 |
| 215 | XNi_vlf1 | Xestia nigrum | chromosome | vlf1 | AAF05239 |
| 216 | PXy_vlf1 | Plutella xylostella | chromosome | vlf1 | AAG27387 |
| 217 | pXO1-132 | Bacillus anthracis | plasmid pXO1 | 132 | D59107 |
| 218 | Tn4555 | Bacteroides fragilis | transposon Tn4555 | int | AAB53787 |
| 219 | DRa_xer | Deinococcus radiodurans | chromosome | xerD | G75636 |
| 220 | BJa_int | Bradyrhizobium japonicum | chromosome | intA | AAF64651 |
| 221 | BHa_orf4 | Bacillus halodurans | chromosome | BH2349 | BAB06068 |
| 222 | pXO1-103 | Bacillus anthracis | plasmid pXO1 | 103 | G59103 |
| 223 | PAe_orf2 | Pseudomonas aeruginosa | chromosome | orf2 | AAG04117 |
| 224 | pLGV440 | Chlamydia trachomatis | plasmid pLGV440 | orf8 | P08788 |

TABLE 1-continued

Recombinases.

| # | Name | Host | Organism | Gene | Accession |
|---|---|---|---|---|---|
| 225 | Tn5520 | *Bacteroides fragilis* | transposon Tn5520 | bipH | AAC80279 |
| 226 | pNL1_tnpA | *Sphingomonas aromaticivorans* | plasmid pNL1 | tnpA | AAD03922 |
| 227 | CTr_orf | *Chlamydia trachomatis* | chromosome | orf1 | S44160 |
| 228 | BHa_orf1 | *Bacillus halodurans* | chromosome | BH3551 | BAB07270 |
| 229 | phi-933W | *Escherichia coli* | phage 933W | int | AAD25406 |
| 230 | CPs_orf1 | *Chlamydia psittaci* | chromosome | orf | B39999 |
| 231 | VCh_orf2 | *Vibrio cholerae* | chromosome | VC1758 | AAF94908 |
| 232 | DRa_orf2 | *Deinococcus radiodurans* | chromosome | orf2 | F75611 |
| 233 | pCPnE1 | *Chlamydophila pneumoniae* | plasmid pCPnE1 | orf2 | CAA57585 |
| 234 | ECo_intB | *Escherichia coli* | chromosome | intB | AAD37509 |
| 235 | UUr_xerC | *Ureaplasma urealyticum* | chromosome | xerC | AAF30630 |
| 236 | HK97 | *Escherichia coli* | phage HK97 | int | AAF31094 |
| 237 | TPW22 | *Lactococcus* sp. | phage TPW22 | int | AAF12706 |
| 238 | APSE-1 | *Acyrthosiphon pisum* | phage APSE-1 | int | AAF03981 |
| 239 | pURB500 | *Methanococcus maripaludis* | plasmid pURB500 | int | AAC45247 |
| 240 | SFl_int | *Shigella flexneri* | chromosome | int | AAD44730 |
| 241 | UUr_xerD | *Ureaplasma urealyticum* | chromosome | ripX | AAF30551 |
| 242 | Wphi | *Escherichia coli* | phage Wphi | int | CAB54522 |
| 243 | BHa_orf2 | *Bacillus halodurans* | chromosome | BH2364 | BAB06083 |
| 244 | SEn_int | *Salmonella enterica* | chromosome | intI5 | AAG03003 |
| 245 | pCP1 | *Deinococcus radiodurans* | plasmid pCP1 | xerD | AAF12667 |
| 246 | SCo_int | *Streptomyces coelicolor* | chromosome | int | CAB71253 |
| 247 | PRi1724 | *Agrobacterium rhizogenes* | plasmid pRi1724 | orf9 | BAB16128 |
| 248 | SCo_traS | *Streptomyces coelicolor* | chromosome | traS | T35465 |
| 249 | HPy_orf1 | *Helicobacter pylori* | chromosome | orf | A71870 |
| 250 | XFa_orf1 | *Xylella fastidiosa* | chromosome | XF2530 | AAF85328 |
| 251 | UUr_codV | *Ureaplasma urealyticum* | chromosome | codV | AAF30942 |
| 252 | pXO1-18 | *Bacillus anthracis* | plasmid pXO1 | 18 | B59093 |
| 253 | CPs_orf2 | *Chlamydia psittaci* | chromosome | orf2 | A39999 |
| 254 | SPBc2 | *Bacillus subtilis* | phage SPBc2 | yopP | T12850 |
| 255 | D3 | *Pseudomonas aeruginosa* | phage D3 | int | AAF04808 |
| 256 | XFa_orf2 | *Xylella fastidiosa* | chromosome | XF1642 | AAF84451 |
| 257 | XFa_orf3 | *Xylella fastidiosa* | chromosome | XF0678 | AAF83488 |
| 258 | pLGV440-2 | *Chlamydia trachomatis* | plasmid pLGV440 | N1 | S01180 |
| 259 | pB171 | *Escherichia coli* | plasmid pB171 | rsvB | BAA84906 |
| 260 | DRa_orf3 | *Deinococcus radiodurans* | chromosome | orf | C75509 |
| 261 | CPZ-55 | *Escherichia coli* | phage CPZ-55 | int | P76542 |
| 262 | ICESt1 | *Streptococcus thermophilus* | transposon ICESt1 | int | CAB70622 |
| 263 | pGP7-D | *Chlamydia trachomatis* | plasmid pGP7-D | TCA01 | AAF39715 |
| 264 | XFa_orf4 | *Xylella fastidiosa* | chromosome | XF1718 | AAF84527 |
| 265 | HIn_orf2 | *Haemophilus influenzae* | chromosome | int | AAF27347 |
| 266 | DNo_orf2 | *Dichelobacter nodosus* | chromosome | intC | CAB57348 |
| 267 | NBU2 | *Bacteroides fragilis* | transposon NBU2 | intN2 | AAF74726 |
| 268 | pColIB | *Shigella sonnei* | plasmid ColIB-P9 | resA | BAA75108 |
| 269 | PSy_orf4 | *Pseudomonas syringiae* | chromosome | orf | CAC14205 |
| 270 | Tn4652 | *Pseudomonas putida* | transposon Tn4652 | orf5 | AAD44277 |
| 271 | pLGV440-3 | *Chlamydia trachomatis* | plasmid pLGV440 | orf7 | P10561 |
| 272 | PF | *Escherichia coli* | plasmid F | int | BAA97902 |
| 273 | BHa_orf3 | *Bacillus halodurans* | chromosome | BH4039 | BAB07758 |
| 274 | XFa_orf5 | *Xylella fastidiosa* | chromosome | XF2132 | AAF84931 |
| 275 | pNRC100_1 | *Halobacterium* sp. | plasmid pNRC100 | H0618 | T08273 |
| 276 | SDy_orf | *Shigella dysenteriae* | chromosome | int | AAF28112 |
| 277 | pQpRS_2 | *Coxiella burnetti* | plasmid pQpRS | orf410 | CAA75839 |
| 278 | PMu_rci | *Pasteurella multocida* | chromosome | rci | AAF68420 |
| 279 | SPBc2 | *Bacillus subtilis* | phage SPBc2 | yomM | AAC13009 |
| 280 | PPa_int | *Pseudomonas pavonaceae* | chromosome | intP | CAB65361 |
| 281 | pKLC102 | *Pseudomonas aeruginosa* | plasmid pKLC102 | xerC | AAG02084 |
| 282 | XFa_orf6 | *Xylella fastidiosa* | chromosome | XF0631 | AAF83441 |
| 283 | SCo_orf3 | *Streptomyces coelicolor* | chromosome | int | CAC14368 |
| 284 | LLa_orf | *Lactococcus lactis* | chromosome | orf3 | AAF86683 |
| 285 | MSp_orf | *Mycobacterium* sp. | chromosome | intM | CAB65286 |
| 286 | pNL1_tnpB | *Sphingomonas aromaticivorans* | plasmid pNL1 | tnpB | AAD03921 |
| 287 | XFa_orf7 | *Xylella fastidiosa* | chromosome | XF0968 | AAF83778 |
| 288 | ECo_orf5 | *Escherichia coli* | chromosome | int | AAF06962 |
| 289 | AGe_vlf1 | *Anticarsia gemmatalis* | chromosome | vlf-1 | AAD54607 |
| 290 | pLH1 | *Lactobacillus helveticus* | plasmid pLH1 | orf195 | CAA10964 |

TABLE 1-continued

Recombinases.

| # | Name | Host | Organism | Gene | Accession |
|---|---|---|---|---|---|
| 291 | SAu_orf2 | *Staphylococcus aureus* | chromosome | orf | AAG29618 |
| 292 | LDi_vlf1 | *Lymantria dispar* | chromosome | vlf-1 | AAC70272 |
| 293 | OPs_vlf1 | *Orgyia pseudotsugata* | chromosome | vlf-1 | AAC59079 |
| 294 | SCo_orf2 | *Streptomyces coelicolor* | chromosome | int | CAC08306 |
| 295 | BBu_orf | *Borrelia burgdorferi* | chromosome | orf6 | AAC34963 |
| 296 | pNOB8 | *Sulfolobus* sp. | plasmid pNOB8 | orf101 | T31031 |
| 297 | pMT1 | *Yersinia pestis* | plasmid pMT1 | T1101 | T15016 |
| 298 | ACa_vlf1 | *Autographica californica* | chromosome | vlf-1 | AAA66707 |
| 299 | VCh_orf3 | *Vibrio cholerae* | chromosome | VC0821 | AAF96190 |
| 300 | BMo_vlf1 | *Bombyx mori* | chromosome | vlf-1 | AAC63749 |
| 301 | phi-PV83 | *Staphylococcus aureus* | phage PV83 | int | BAA97808 |
| 302 | PGi_orf | *Porphyromonas gingivalis* | chromosome | orf6 | BAA35089 |
| 303 | AFu_orf | *Archaeoglobus fulgidus* | chromosome | AF0082 | B69260 |
| 304 | pCHL1 | *Chlamydia trachomatis* | plasmid pCHL1 | orf7 | AAA91567 |
| 305 | pR27 | *Salmonella typhi* | plasmid R27 | orf | AAF70020 |
| 306 | APe_orf | *Aeropyrum pernix* | chromosome | APE0818 | E72674 |
| 307 | PSy_orf2 | *Pseudomonas syringiae* | chromosome | orfA | CAB96965 |
| 308 | pNRC100_2 | *Halobacterium* sp. | plasmid pNRC100 | H0928 | T08297 |
| 309 | MJa_orf2 | *Methanococcus jannaschi* | chromosome | MJ0770 | Q58180 |
| 310 | phi16-3 | *Rhizobium* sp. | phage 16-3 | int | CAB54831 |
| 311 | pCP32-1 | *Borrelia burgdorferi* | plasmid cp-1 | BBP37 | AAF07426 |
| 312 | SAl_orf | *Streptomyces albus* | chromosome | orf | AAD46512 |
| 313 | pNRC100_3 | *Halobacterium* sp. | plasmid pNRC100 | H1373 | T08333 |
| 314 | VCh_orf4 | *Vibrio cholerae* | chromosome | VC0185 | AAF93361 |
| 315 | Tec2 | *Euplotes crassus* | transposon Tec2 | orf2B | AAA91341 |
| 316 | Tec1 | *Euplotes crassus* | transposon Tec1 | orf2B | AAA91341 |
| 317 | PPu_orf3 | *Pseudomonas putida* | chromosome | orf101 | CAB54061 |
| 318 | pCP32 | *Borrelia hermsii* | plasmid cp32 | orf6 | AAF28881 |
| 319 | NMe_int | *Neisseria meningitidis* | chromosome | int | CAB84481 |
| 320 | pCP32-4 | *Borrelia burgdorferi* | plasmid cp32-4 | BBR38 | AAF07512 |
| 321 | pCP18 | *Borrelia burgdorferi* | plasmid cp18 | orf6 | AAB63432 |
| 322 | pCP18-2 | *Borrelia burgdorferi* | plasmid cp18-2 | orf27 | AAF29799 |
| 323 | Tn5401 | *Bacillus thuringensis* | transposon Tn5401 | int | P27451 |
| 324 | SMi_xerD | *Streptococcus mitis* | chromosome | xerD | CAC19443 |
| 325 | SPn_xerD | *Streptococcus pneumoniae* | chromosome | xerD | CAC19448 |
| 326 | EFa_orf | *Enterococcus faecium* | chromosome | intD | AAG42074 |
| 327 | VT1 | *Escherichia coli* O157:H7 | phage VT1-Sakai | int | BAB19626 |
| 328 | psiM100 | *Methanothermobacter wolfeii* | phage psiM100 | int | AAG39942 |
| 329 | CP-933C | *Escherichia coli* O157:H7 | phage 933C | Z1835 | AAG55933 |
| 330 | CP-933I | *Escherichia coli* O157:H7 | phage 933I | Z0324 | AAG54584 |
| 331 | CP-933M | *Escherichia coli* O157:H7 | phage 933M | Z1323 | AAG55457 |
| 332 | CP-933U | *Escherichia coli* O157:H7 | phage 933U | intU | AAG57039 |
| 333 | CP-933T | *Escherichia coli* O157:H7 | phage 933T | intT | AAG56898 |
| 334 | CP-933N | *Escherichia coli* O157:H7 | phage 933N | intN | AAG55869 |
| 335 | CP-933O | *Escherichia coli* O157:H7 | phage 933O | intO | AAG56112 |
| 336 | bIL310 | *Lactococcus lactis* | phage bIL310 | orf1 | AAK08405 |
| 337 | bIL311 | *Lactococcus lactis* | phage bIL311 | int | AAK08433 |
| 338 | SPy_orf5 | *Streptococcus pyogenes* | chromosome | int4 | AAK34767 |
| 339 | bIL309 | *Lactococcus lactis* | phage bIL309 | int | AAK08349 |
| 340 | bIL312 | *Lactococcus lactis* | phage biL312 | int | AAK08454 |
| 341 | SPy_orf2 | *Streptococcus pyogenes* | chromosome | int3 | AAK33851 |
| 342 | SPy_orf4 | *Streptococcus pyogenes* | chromosome | int2 | AAK34288 |
| 343 | bIL286 | *Lactococcus lactis* | phage bIL286 | int | AAK08288 |
| 344 | LLa_xerD | *Lactococcus lactis* | chromosome | xerD | AAK04743 |
| 345 | LLa_ymfD | *Lactococcus lactis* | chromosome | ymfD | AAK05330 |
| 346 | SPy_orf3 | *Streptococcus pyogenes* | chromosome | spy1196 | AAK34058 |
| 347 | SPy_orf1 | *Streptococcus pyogenes* | chromosome | spy0365 | AAK33410 |
| 348 | LLa_orf2 | *Lactococcus lactis* | chromosome | ynbA | AAK05376 |
| 349 | ECo_orf7 | *Escherichia coli* O157:H7 | chromosome | Z4313 | AAG58098 |
| 350 | ECo_orf6 | *Escherichia coli* O157:H7 | chromosome | Z1120 | AAG55265 |
| 351 | pMLa | *Mesorhizobium loti* | plasmid pMLa | mll9356 | BAB54967 |
| 352 | pMLb | *Mesorhizobium loti* | plasmid pMLb | mlr9649 | BAB54839 |
| 353 | pRi_orf2 | *Rhizobium rhizogenes* | plasmid pRi | ril36 | BAB16255 |
| 354 | MLo_orf1 | *Mezorhizobium loti* | chromosome | mll8495 | BAB54366 |
| 355 | MLo_orf2 | *Mezorhizobium loti* | chromosome | mll7973 | BAB53631 |
| 356 | MLo_orf3 | *Mezorhizobium loti* | chromosome | mlr7741 | BAB54140 |
| 357 | MLo_orf4 | *Mezorhizobium loti* | chromosome | mlr6952 | BAB53138 |
| 358 | SEn_orf2 | *Salmonella enterica* | chromosome | int2 | AF261825 |
| 359 | MLo_orf5 | *Mezorhizobium loti* | chromosome | mll5763 | BAB52151 |
| 360 | ECo_orf8 | *Escherichia coli* | chromosome | ILG1 | AAK49816 |
| 361 | MLo_orf6 | *Mezorhizobium loti* | chromosome | mlr0958 | BAB48432 |
| 362 | CCr_orf1 | *Caulobacter crescentus* | chromosome | CC2681 | AAK24647 |

TABLE 1-continued

Recombinases.

| # | Name | Host | Organism | Gene | Accession |
|---|------|------|----------|------|-----------|
| 363 | MLo_orf7 | *Mezorhizobium loti* | chromosome | mll4043 | BAB50796 |
| 364 | MLo_orf8 | *Mezorhizobium loti* | chromosome | mll0487 | BAB48065 |
| 365 | MLo_orf9 | *Mezorhizobium loti* | chromosome | mlr0475 | BAB48054 |
| 366 | phi-ETA | *Staphylococcus aureus* | phage phi-ETA | orf1 | BAA97587 |
| 367 | CCr_xerD | *Caulobacter crescentus* | chromosome | CC3006 | AAK24968 |
| 368 | CCr_xerC | *Caulobacter crescentus* | chromosome | CC0344 | AAK22331 |
| 369 | pRVS1 | *Vibrio salmonicida* | plasmid pRVS1 | int | CAC35342 |
| 370 | phiSLT | *Staphylococcus aureus* | phage phi-SLT | int | BAB21695 |
| 371 | SSo_xer | *Sulfolobus solfataricus* | chromosome | xerCD | AAK40704 |
| 372 | CW459 | *Clostridium perfringens* | transposon CW459 | int459 | AAK17958 |
| 373 | MPu_xerC | *Mycoplasma pulmonis* | chromosome | MY5310 | CAC13704 |
| 374 | TVo_xerC | *Thermoplasma volcanium* | chromosome | xerC | BAB59407 |
| 375 | TAc_xerC | *Thermoplasma acidophilum* | chromosome | Tal314 | CAC12435 |
| 376 | TVo_orf1 | *Thermoplasma volcanium* | chromosome | orf1 | BAB59869 |
| 377 | SEn_orf2 | *Salmonella enterica* | chromosome | S020 | AAK02039 |
| 378 | PMu_xerC | *Pasteurella multocida* | chromosome | xerC | AAK03785 |
| 379 | PMu_xerD | *Pasteurella multocida* | chromosome | xerD | AAK02177 |
| 380 | MLo_xerD | *Mesorhizobium loti* | chromosome | mlr3575 | NP_104652 |
| 381 | DRa_orf4 | *Deinococcus radiodurans* | chromosome | xerD | AAF12544 |
| 382 | HSp_orf1 | *Halobacterium* sp. | chromosome | ssrA | AAG19292 |
| 383 | PMu_orf1 | *Pasteurella multocida* | chromosome | slpA | AAK03853 |
| 384 | PGi_xerC | *Porphyromonas gingivalis* | chromosome | PG1732 | |
| 385 | PGi_xerD | *Porphyromonas gingivalis* | chromosome | PG0386 | |
| 386 | RCa_orf3 | *Rhodobacter capsulatus* | chromosome | orf | U57682 |
| 387 | MLo_orf10 | *Mesorhizobium loti* | chromosome | mlr9321 | NP_085850 |
| 388 | MLo_orf11 | *Mesorhizobium loti* | chromosome | mlr9323 | NP_085851 |
| 389 | MLo_orf12 | *Mesorhizobium loti* | chromosome | mlr9324 | NP_085852 |
| 390 | MLo_orf13 | *Mesorhizobium loti* | chromosome | mll9328 | NP_085856 |
| 391 | MLo_orf14 | *Mesorhizobium loti* | chromosome | mll9329 | NP_085857 |
| 392 | MLo_orf15 | *Mesorhizobium loti* | chromosome | mll9330 | NP_085858 |
| 393 | MLo_orf16 | *Mesorhizobium loti* | chromosome | mll9331 | NP_085859 |

In some embodiments, the suitable recombinase is a recombinases selected from the group consisting of recombinases listed as numbers 7, 12, 93, 95, 97, and 98 in Table 1.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a yeast cell cultured under suitable conditions. The promoters and control sequences are specific for each yeast cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, Xho1, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual nucleic acid sequences may be "spliced" together and subsequently transduced into a yeast microorganism simultaneously. Thus, expression of each of the plurality of nucleic acid sequences is effected.

In some embodiments, the yeast cells of the present invention are genetically modified in that heterologous nucleic acid have been introduced into the yeast cells, and as such the genetically modified yeast cells do not occur in nature. The suitable yeast cell is one capable of expressing a nucleic acid construct encoding the enzyme(s) described herein. The gene encoding the enzyme may be heterologous to the yeast cell or the gene may be native to the yeast cell but is operatively linked to a heterologous promoter and one or more control regions which result in a higher expression of the gene in the yeast cell. Each enzyme described herein can be native or heterologous to the yeast cell. Where the enzyme is native to the yeast cell, the yeast cell is genetically modified to modulate expression of the enzyme. This modification can involve the modification of the chromosomal gene encoding the enzyme in the yeast cell or a nucleic acid construct encoding the gene of the enzyme is introduced into the yeast cell. One of the effects of the modification is the expression of the enzyme is modulated in the yeast cell, such as the increased expression of the enzyme in the yeast cell as compared to the expression of the enzyme in an unmodified yeast cell.

The system's ability to provide inducible and dynamic regulation of gene regulation is highly desirable especially in certain cases. For example, the system is desirable when the product, or intermediate products in the product pathway, are toxic and lead to growth arrest if expressed constitutively and during the early stage of growth (Brockman and Prather 2015; Martin et al. 2003).

In another example, the system is desirable when the product, or intermediate products, require a high amount of cellular resources such as ATP or redox factors, leading to non-optimal growth and decreased productivity if expressed constitutively and during the early stage of growth (Brockman and Prather 2015; Moon et al. 2009).

Currently, the use of inducible promoters in *Saccharomyces cerevisiae* (Hubmann et al. 2014) has certain disadvantages:

For example, for the GAL promoter, wherein the promoter is induced by growth in galactose. Cells have to be grown on raffinose followed by growth on galactose for optimal induction. The presence of glucose inhibits expression (Hubmann et al. 2014).

For example, for the Sucrose promoter, wherein the use of this promoter requires the use special media containing sucrose, which does not scale well (Williams et al. 2015).

For example, for the CUP promoter, wherein this promoter is induced by addition of copper. Addition of an external inducer increases the production cost. Furthermore, copper is toxic to the environment and effluent is regulated.

For example, for the DAN promoter, wherein this promoter is induced by oxygen depletion. The DAN promoter is not suitable for products that are produced by 'oxygen-dependent' metabolism.

For example, for promoters induced through exogenous addition of aromatic amino acids, such as tryptophan. Similar to the promoters induced by galactose, these promoters require a special growth procedure, as experiments show the need for subculture from logarithmic phase (Leavitt et al. 2016).

For example, for temperature sensitive promoters, wherein these promoters are induced and repressed at specific temperatures, which may not be optimal to use for growth and production in a yeast cell. It is difficult to regulate, maintain and shift temperatures in large bioprocesses, especially in fermenters used for large scale production where temperature heterogeneity is common (Neubauer and Junne 2010).

In some embodiments, the tetracycline-inducible promoter, wherein the promoter is induced by addition or removal of tetracycline (or analogue thereof) to the fermenter. The addition of an external inducer increases the production cost.

There are several advantages to the present invention:

In some embodiments, any type of media where the cell can grow in can be used, since the induction signal is density-dependent and gene expression will be activated when the culture reaches a certain OD.

In some embodiments, due to the intrinsic function of our system, no inducer needs to be added to the main culture, which decreases production cost compared to systems where inducer has to be added.

In some embodiments, different promoter strengths can be used for expressing the pathway or protein during production, which for example enables pathway balancing.

The system can be used for the inducible and dynamic regulation of expression of any biochemical pathway or any protein. In some embodiments, the system can be used to produce compounds that are toxic to the production organism, as the system allows for a build-up of cell mass before starting production of the toxic biochemical or protein. The system can be used to produce to pharmaceuticals and valuable chemicals that are derived from pathways that have toxic intermediates, such as the mevalonate pathway.

In some embodiments, the system comprises a plurality of genes of interest (GOIs) wherein at least 2, 3, 4, or more, or all of each GOI is separately operatively linked to a separate and different promoter that is activated by the α-factor receptor bound to the α-factor. In some embodiments, the separate promoters are derived or obtained from a single pathway. Such a system allows for dynamic induction of a balanced pathway, a major advance in autoinduction. In some embodiments, instead of a stop codon, the system can switch from expressing one or several genes before the recombinase activates the expression of another gene or genes. For example, in some embodiments, if there is a toxic buildup of a product when using constitutive promoters, one approach is to produce the downstream, non-toxic metabolites during the "OFF" phase. Once the "ON" phase is reached, the yeast can switch to produce the upstream components containing the toxic metabolite(s), which is then rapidly consumed by the downstream components that are already built up.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

An Autoinducible Gene Expression System for *Saccharomyces cerevisiae*

Herein is described an engineered novel auto-inducible expression system for *S. cerevisiae* based on its native mating response. A circuit with two different plasmids is established; an input plasmid harboring the Cre recombinase under control of the pFUS1 promoter or versions of it, and several output plasmids harboring the production gene of interest. After optimizing the Cre recombinase expression levels, it is shown that the system inducible by external addition of α-factor and that it is both tunable and titratable. It is further established a range of autoinducible strains with variable induction patterns by integrating the MFα1 and STE2 genes under different promoters. To control and prevent autoinduction after transformation and during pre-culturing, an inducible control module is engineered to comprise the α-factor-degrading protease Bar1 and introducing it into our input plasmid to prevent induction. Finally, two positive feedback loops are engineered on the input plasmid to optimize expression levels of the autoinducible strains.

Materials and Methods

Media and Materials

Lysogeny broth agar plates (LB, 10 g/L tryptone, 5 g/L yeast extract, 10 g/L NaCl, 50 µg/mL carbenicillin) and media is used for cultivation and screening during cloning. Yeast peptone dextrose (YPD, 20 g/L bacto peptone, 10 g/L yeast extract, 2 g/L glucose) and Complete Synthetic Media (CSM, 6.7 g/L yeast nitrogen base without amino acids with ammonium sulfate, 0.77 g/L of appropriate amino acid drop-out mix, 2 g/L glucose) is used for cultivation and strain characterization. Bacto agar is added for plates.

Chemicals that are used in the study were purchased from Sigma-Aldrich (St Louis, MO, USA) and restriction enzymes and PCR polymerases are purchased from Thermo Fischer Scientific (Waltham, MA, USA) or NEB (Ipswich, MA, USA).

Plasmid and Strain Construction

The primers used in this study are ordered from Integrated DNA Technologies (Coralville, IA, USA). Plasmids are constructed by Gibson assembly (Gibson, D. G., Young, L., Chuang, R.-Y., Venter, J. C., Hutchison, C. A., & Smith, H. O. (2009). Enzymatic assembly of DNA molecules up to several hundred kilobases. *Nature Methods*, 6(5), 343-345). *Escherichia coli* MegaX DH10β TI® Electrocomp™ cells from Thermo Fischer Scientific (Waltham, MA, USA) is used for plasmid cloning and propagation. Plasmid purification is carried out with the QIAprep Spin Miniprep kit from Qiagen (Hilden, Germany) and cell transformation is carried out using electroporation for *Escherichia coli* and the Frozen-EZ Yeast Transformation II Kit from Zymo Research (Irvine, CA, USA) for *S. cerevisiae*.

Yeast strains are constructed using CRISPR according to the protocol described by Apel et al. (Apel A. R., Espaux, L., Wehrs, M., Sachs, D., Li, A., Tong, G. J., . . . Mukhopadhyay, A. (2017). A Cas9-based toolkit to program gene expression in *Saccharomyces cerevisiae*. *Nucleic Acids Research*, 45(1), 496-508). Briefly, integration or knock-out strains are prepared by transforming the parental strain with a pCUT plasmid harboring a constitutively expressed Cas9 and sgRNA targeting the integration or knock-out site, and cassettes with 30-60 bp internal overlap and 500 bp overlap to the genomic integration or knock-out locus. A concentration of 500 ng of each fragment and 500 ng of plasmid are used for transformation. Correct constructs are confirmed by colony PCR. Plates supplemented with 5-fluoroorotic acid are used for plasmid curing of the pCUT plasmid. All strains and plasmids used in the study are listed in Table 2.

TABLE 2

Strains and plasmids used in the study. Names used to refer to strains or plasmids in text are marked in bold.

| Strain | Description | Reference/source |
| --- | --- | --- |
| MegaX DH10β TI$^R$ | Cloning strain | Thermo Fischer Scientific |
| BY474 | MATa his3Δ1 leu2Δ0 met15Δ0 ura3Δ0 | Lab collection |
| JL275 | JL275 BY4741 bar1Δ far1Δ | This study |
| JL276 | JL276 BY4741 Δbar1 Δfar1 Δste2 | This study |
| JL277 | JL277 BY4741 Δbar1 Δfar1 Δste2 416d::pTDH3-MFα1 | This study |
| JL278 | JL278 BY4741 Δbar1 Δfar1 Δste2 416d::pPGK1-MFα1 | This study |
| JL279 | JL279 BY4741 Δbar1 Δfar1 Δste2 416d::pYEF3-MFα1 | This study |
| JL280 | JL280 BY4741 Δbar1 Δfar1 Δste2 416d::pACT1-MFα1 | This study |
| JL281 | JL281 BY4741 Δbar1 Δfar1 Δste2 416d::pTDH3-STE2 | This study |
| JL282 | JL282 BY4741 Δbar1 Δfar1 Δste2 416d::pPGK1-STE2 | This study |
| JL283 | JL283 BY4741 Δbar1 Δfar1 Δste2 416d::pYEF3-STE2 | This study |
| JL284 | JL284 BY4741 Δbar1 Δfar1 Δste2 416d::pACT1-STE2 | This study |
| JL286 | JL286 BY4741 Δbar1 Δfar1 Δste2 1021b::pTDH3-STE2 416d::pTDH3-MFα1 | This study |
| JL287 | JL287 BY4741 Δbar1 Δfar1 Δste2 1021b::pPGK1-STE2 416d::pTDH3-MFα1 | This study |
| JL288 | JL288 BY4741 Δbar1 Δfar1 Δste2 1021b::pYEF3-STE2 416d::pTDH3-MFα1 | This study |
| JL289 | JL289 BY4741 Δbar1 Δfar1 Δste2 1021b::pACT1-STE2 416d::pTDH3-MFα1 | This study |
| JL290 | JL290 BY4741 Δbar1 Δfar1 Δste2 1021b::pTDH3-STE2 416d::pPGK1-MFα1 | This study |
| JL291 | JL291 BY4741 Δbar1 Δfar1 Δste2 1021b::pPGK1-STE2 416d::pPGK1-MFα1 | This study |
| JL292 | JL292 BY4741 Δbar1 Δfar1 Δste2 1021b::pYEF3-STE2 416d::pPGK1-MFα1 | This study |
| JL293 | JL293 BY4741 Δbar1 Δfar1 Δste2 1021b::pACT1-STE2 416d::pPGK1-MFα1 | This study |

TABLE 2-continued

Strains and plasmids used in the study. Names used to refer to strains or plasmids in text are marked in bold.

| | | |
|---|---|---|
| JL294 | JL294 BY4741 Δbar1 Δfar1 Δste2 1021b::pTDH3-STE2 416d::pYEF3-MFα1 | This study |
| JL295 | JL295 BY4741 Δbar1 Δfar1 Δste2 1021b::pPGK1-STE2 416d::pYEF3-MFα1 | This study |
| JL296 | JL296 BY4741 Δbar1 Δfar1 Δste2 1021b::pYEF3-STE2 416d::pYEF3-MFα1 | This study |
| JL297 | JL297 BY4741 Δbar1 Δfar1 Δste2 1021b::pACT1-STE2 416d.::pYEF3-MFα1 | This study |
| JL298 | JL298 BY4741 Δbar1 Δfar1 Δste2 1021b::pTDH3-STE2 416d::pACT1-MFα1 | This study |
| JL299 | JL299 BY4741 Δbar1 Δfar1 Δste2 1021b::pPGK1-STE2 416d::pACT1-MFα1 | This study |
| JL300 | JL300 BY4741 Δbar1 Δfar1 Δste2 1021b::pYEF3-STE2 416d::pACT1-MFα1 | This study |
| JL301 | JL301 BY4741 Δbar1 Δfar1 Δste2 1021b::pACT1-STE2 416d::pACT1-MFα1 | This study |

| Plasmid | Description | Reference/source |
|---|---|---|
| pRS416 | Centromeric plasmid | |
| pESC | 2μ plasmid | |
| pJL122 | pTEF1-loxP-GFP-loxP-mCherry: pESC-pTEF1-loxP-GFP-loxP-mCherry | This study |
| pJL123 | pESC pGAL-mCherry | This study |
| pJL124 | pESC pTEF1-mCherry | This study |
| pJL130 | pFUS1-Cre: pRS416 pFUS1-Cre-tHXT7 | This study |
| pJL131 | pFUS1-ubiM-Cre: pRS416 pFUS1-ubiM_Cre-tHXT7 | This study |
| pJL132 | pFUS1J2-Cre: pRS416 pFUS1J2-Cre-tHXT7 | This study |
| pJL133 | pFUS1J2-ubiM-Cre: pRS416 pFUS1J2-ubiM_Cre-tHXT7 | This study |
| pJL134 | pCUT_416d | (Apel et al., 2017) |
| pJL135 | pCUT_1021b | (Apel et al., 2017) |
| pJL136 | pCUT_FAR1 | This study |
| pJL137 | pCUT_STE2 | This study |
| pJL138 | pFUS1J2-ubiM-Cre pTDH3-rtTA pTETO3-BAR1: pRS416 pFUS1J2-ubiM-Cre-tHXT7 pTDH3-rTetRG72V-tSTE2 pTETO3-BAR1-tADE2 | This study |
| pJL139 | pRS416 pFUS1-mCherry | This study |
| pJL140 | pRS416 pFUS1J2-ubiM-mCherry | This study |
| pJL141 | pFUS1J2-ubiM-Cre pTDH3-rtTA pTETO3-BAR1 pFUS1J2-MFα1: pRS416 pFUS1J2-MFalpha1 pFUS1J2-ubiM-Cre-tHXT7 pTDH3-rTetRG72V-tSTE2 pTETO3-BAR1-tADE2 | This study |
| pJL142 | pFUS1J2-ubiM-Cre pTDH3-rtTA pTETO3-BAR1 pTDH3-MFα1: pRS416 pTDH3-MFalpha1 pFUS1J2-MFalpha1 pFUS1J2-ubiM-Cre-tHXT7 pTDH3-rTetRG72V-tSTE2 pTETO3-BAR1-tADE2 | This study |
| pJL143 | pCUT_BAR1 | This study |
| pJL144 | pTDH3-loxP-GFP-loxP-mCherry: pESC pTDH3-loxP-GFP-loxP-mCherry | This study |
| pJL145 | pHHF2-loxP-GFP-loxP-mCherry: pESC pHHF2-loxP-GFP-loxP-mCherry | This study |
| pJL146 | pHSP26-loxP-GFP-loxP-mCherry: pESC pHSP26-loxP-GFP-loxP-mCherry | This study |
| pJL147 | pHXT7-loxP-GFP-loxP-mCherry: pESC pHXT7-loxP-GFP-loxP-mCherry | This study |

Strain Characterization

Pre-cultures are prepared by inoculation of biological triplicates in CSM with appropriate amino acid drop out, and are grown for two days at 30° C., 250 rpm. Thereafter, they are inoculated to an OD of 0.05 in two duplicate tubes, whereof one is induced with 5 μM α-factor. Strains are grown at 30° C., 250 rpm for 24 h and samples are taken for flow cytometry after 0, 8 and 24 h. For characterization of strains with endogenous α-factor production, transformation plates and pre-culture media is supplemented with 5 μg/mL doxycycline. The pre-cultures are washed to remove Bar1 and doxycycline prior to inoculation. OD is measured at 600 nm and GFP and mCherry production is measured with a BD Accuri™ C6 flow cytometer from Becton, Dickinson and Company (Franklin Lakes, NJ, USA).

Results and Discussion

Construction of an Autoinducible Expression System in *Saccharomyces cerevisiae*

Figure 1B:
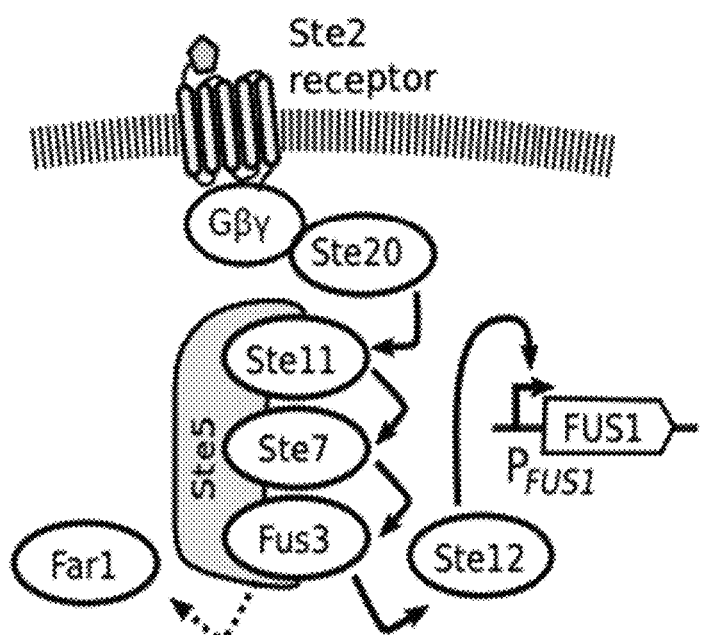
FIG. 1B shows mating response pathway.
Figure 1C:
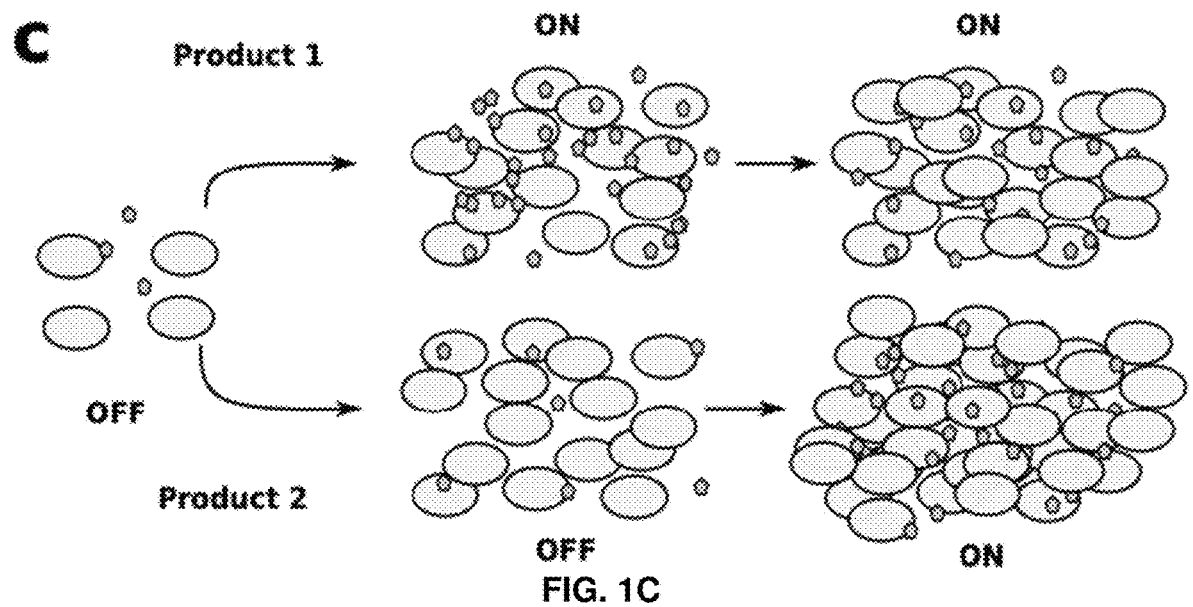
FIG. 1C shows a cell-density dependent autoinducible induction.
Figure 1D:
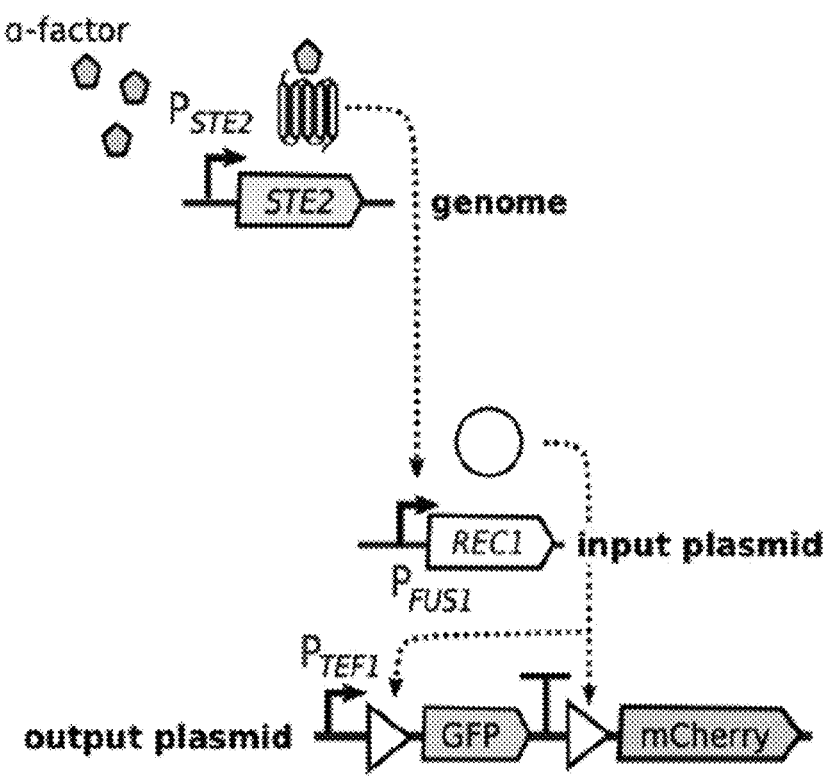
FIG. 1D shows a particular embodiment of the invention, wherein the invention comprises α-factor is added exogenously that results in pFus activation of the Cre recombinase, which excises GFP to produce mCherry.
Figure 1E:
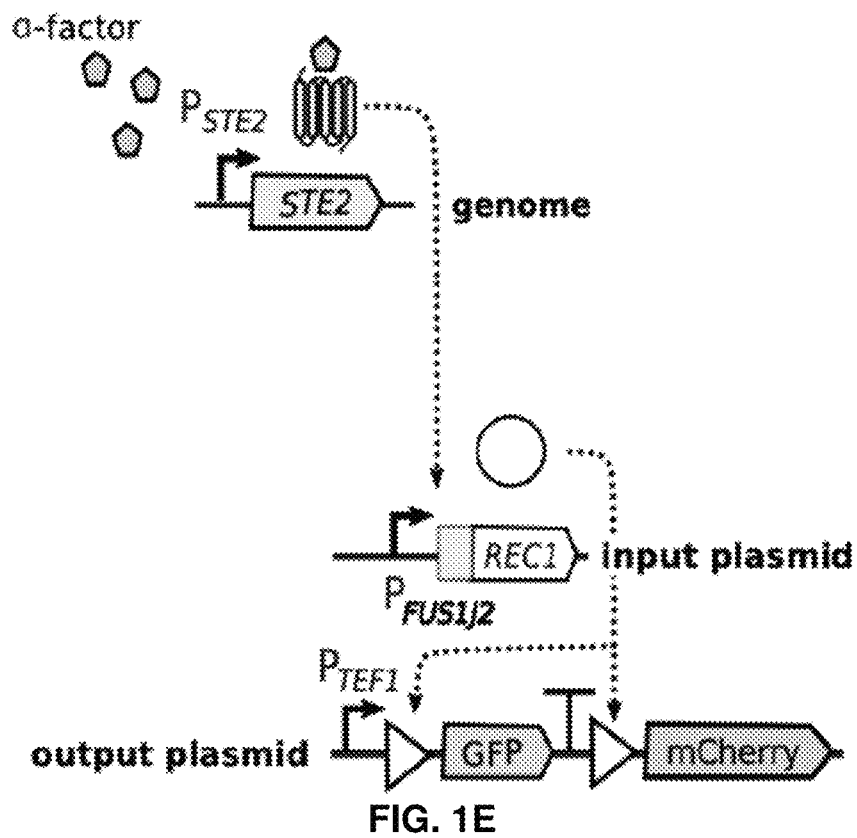
FIG. 1E shows a particular embodiment of the invention, wherein the invention comprises a protein degradation tag on the recombinase and an improved pFUS promoter.
Figure 1F:
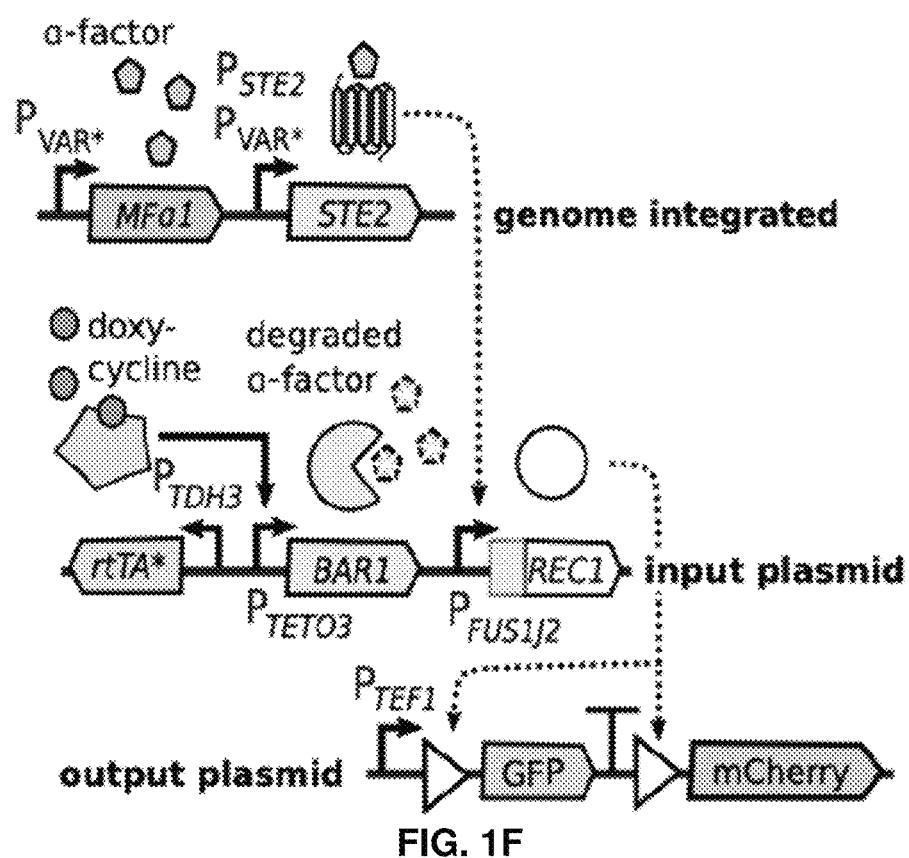
FIG. 1F shows a particular embodiment of the invention, wherein the invention comprises α-factor produced by varying promoters (Pvar) allowing tunable activation of protein expression. A control system based on Ptet is used to control premature activation, as doxycycline is used to produce the protease BAR1 during the preculture period.

In nature, yeast mating is induced by the binding of α-factor, produced by MATα cells, to the Ste2 receptor, expressed in MATα cells (FIG. 1A). When a certain threshold of α-factor is reached, binding to the receptor leads to induction of a MAPK-mediated response pathway that activates transcription factor Ste12, which in turn binds and enables expression from the FUS1 promoter (pFUS1) (FIG. 1B). To utilize the native response mechanism, pFUS1 is rewired to control a Cre recombinase placed on a pRS416 centromeric input plasmid. Upon Cre recombinase expression, a recombinase-based removal of a STOP codon is performed on and output plasmid, enabling expression of the gene(s) of interest (GOI) cloned after the stop codon. (FIG. 1B). This enables a cell-density dependent system transition from an "OFF" to an "ON" state, as a higher cell density will lead to higher amounts of α-factor if the α-factor is produced endogenously (FIG. 1C). To facilitate screening of system functionality, the initial output plasmid is designed and cloned to harbor promoter pTEF1 followed by two loxP site with a GFP-STOP cassette in between, and an mCherry expression gene afterwards (pTEF1-loxP-GFP-loxP-mCherry) (FIG. 1D). In this way, cell population pre- and post recombination event can easily be monitored by measuring GFP and mCherry production using flow cytometry. All plasmid engineering efforts taken in during the course of the study can be seen in FIGS. 1D to 1F, except introduction of the positive feedback loops which are described further down in the results section.

Establishing System Functionality with External Addition of α-Factor

Figure 2A:
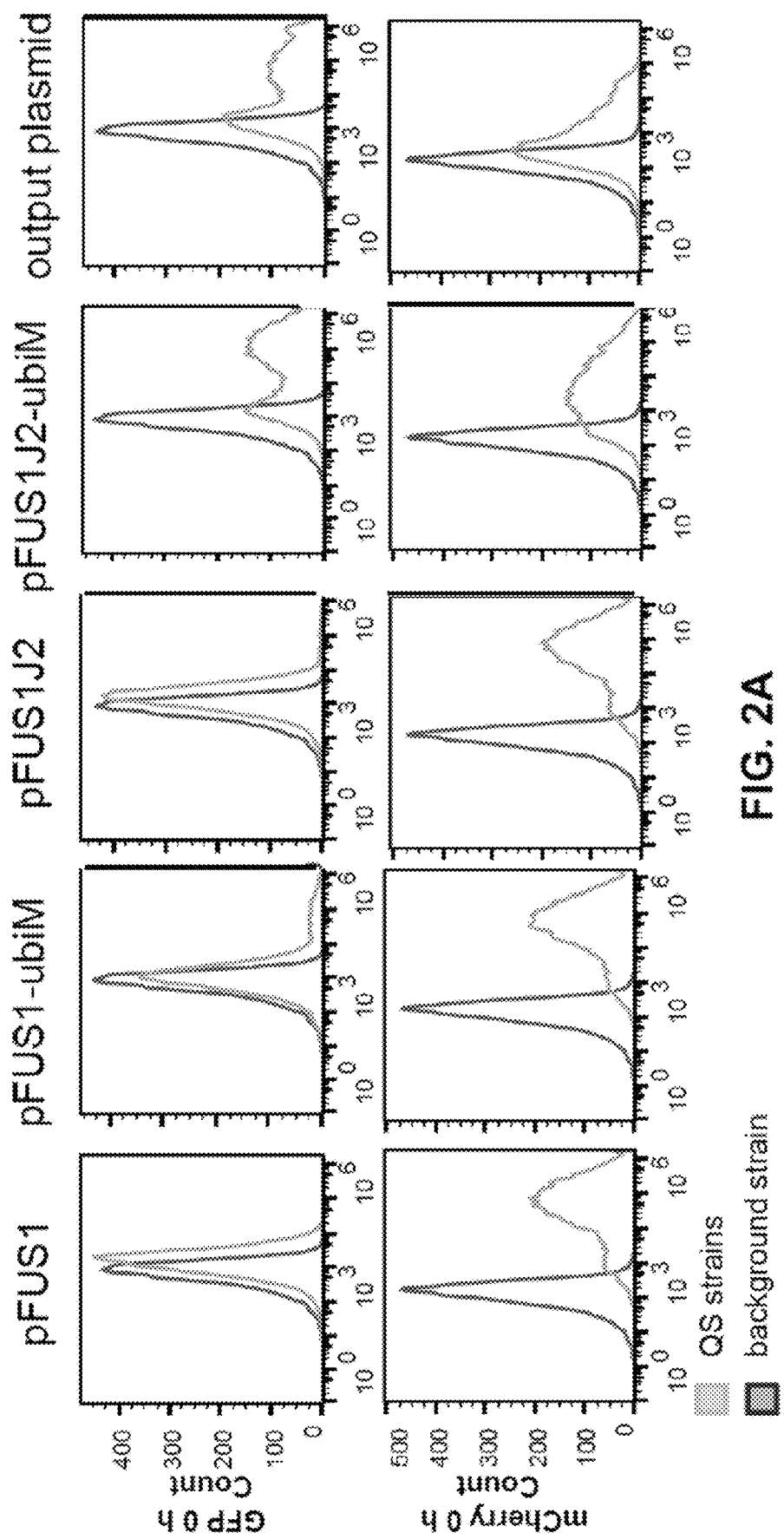
FIG. 2A shows histograms of GFP and mCherry production at 0 h in QS strain JL275 harboring the different input plasmid versions pFUS1-, pFUS1-ubiM-, pFUS1J2-, and pFUS1J2-ubiM-Cre, and/or output plasmid pTEF1-loxP-GFP-loxP-mCherry. Production levels after 0 h (pre-cultures) in QS strains (blue). The red histograms display JL275 autofluorescence. The histograms are a representative sample out of three or more biological replicates.
Figure 2B:
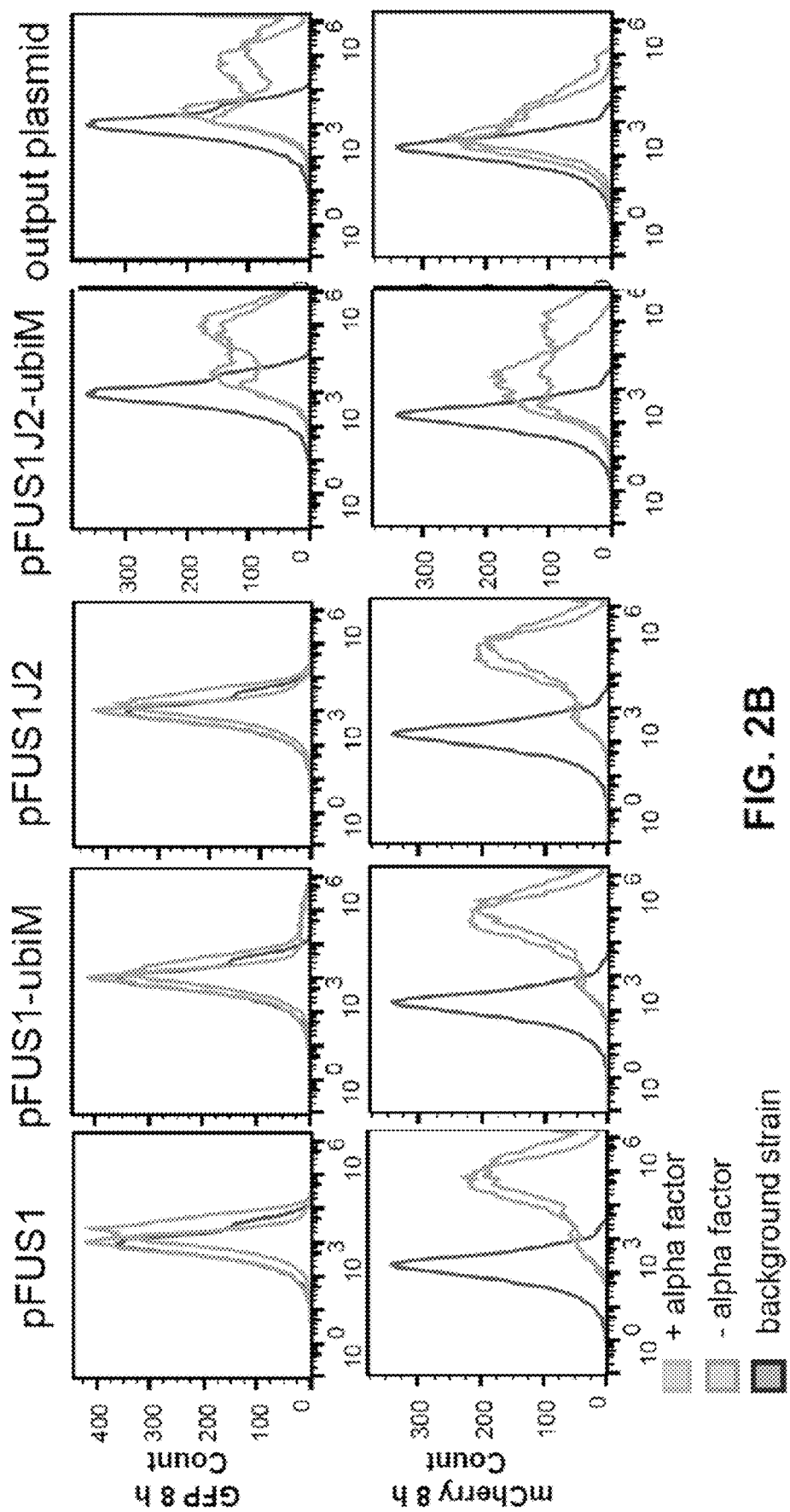
FIG. 2B shows histograms of GFP and mCherry production at 8 h in QS strain JL275 harboring the different input plasmid versions pFUS1-, pFUS1-ubiM-, pFUS1J2-, and pFUS1J2-ubiM-Cre, and/or output plasmid pTEF1-loxP-GFP-loxP-mCherry. Production levels after 8 h, with (blue) or without (orange) addition of 5 μM α-factor. The red histograms display JL275 autofluorescence. The histograms are a representative sample out of three or more biological replicates.
Figure 2C:
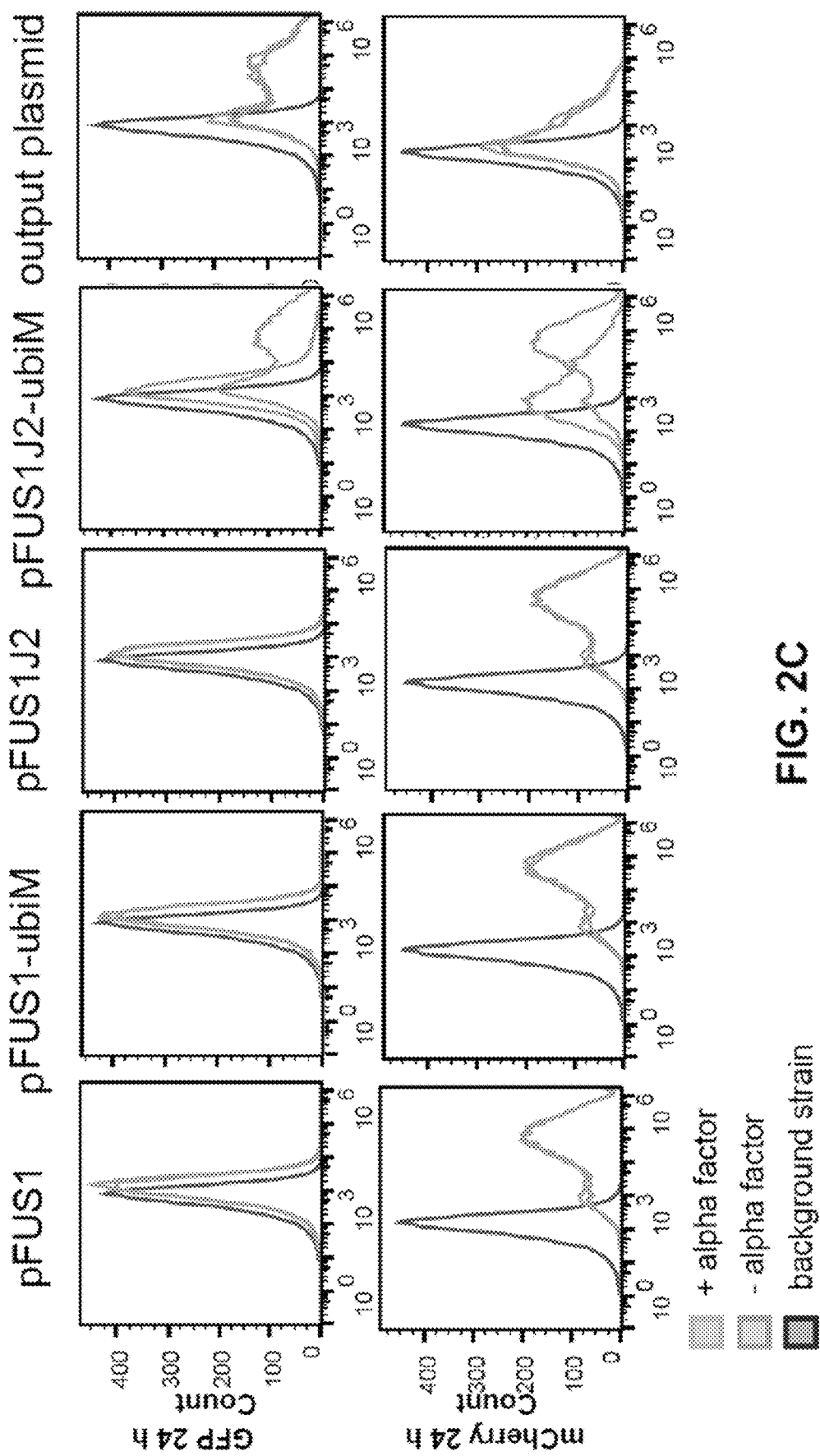
FIG. 2C shows histograms of GFP and mCherry production at 24 h in QS strain JL275 harboring the different input plasmid versions pFUS1-, pFUS1-ubiM-, pFUS1J2-, and pFUS1J2-ubiM-Cre, and/or output plasmid pTEF1-loxP-GFP-loxP-mCherry. Production levels after 24 h, with (blue) or without (orange) addition of 5 μM α-factor. The red histograms display JL275 autofluorescence. The histograms are a representative sample out of three or more biological replicates.

To test the initial system configuration, pFUS1-Cre and pTEF1-loxP-GFP-loxP-mCherry is transformed into strain JL275 (BY4741 MATa Δbar1 Δfar1). Precultures are grown for two days in CSM-ura-leu. Each replicate is used to inoculate two cultures, whereof one is induced with 5 μM α-factor. Fluorescence is measured after 0, 8 and 24 h. Results showed that the system is not working optimally, as mCherry is expressed already at timepoint 0 h, and continuously throughout the cultivation also without addition of α-factor (FIGS. 2A to 2C). This indicated a high basal level expression from the FUS1 promoter, leading to leaky expression of Cre recombinase and early recombination. To investigate this hypothesis, mCherry is cloned under control of pFUS1 and mCherry expression is measured at 0 and 24 h. After pre-culturing, significant levels of mCherry could be seen, with expression being 8-fold higher than the background strain autofluorescence. After 24 h, expression from the promoter is approximately 20-fold and 6-fold higher compared to the background strain autofluorescence in the culture with or without addition of 5 μM α-factor, respectively.

To optimize the system, a lower basal level promoter (pFUS1J2) and a degradation tag (ubiM) is introduced both singly and in combination to control the Cre recombinase expression. Plasmids pFUS1J2-Cre, pFUS1-ubiM-Cre and pFUS1J2-ubiM-Cre are transformed into JL275 together with pTEF1-loxP-GFP-loxP-mCherry, and the strains are characterized in the same way as pFUS1-Cre. Results showed that, while the first two new versions did not show any difference in expression pattern compared to pFUS1-Cre (FIGS. 2A to 2C) the combination of a degradation tag and a lower basal level expression promoter significantly improved system performance (FIGS. 2A to 2C). A clear shift from GFP to mCherry production can be seen only if α-factor is added to the media, and if not, GFP is stably expressed through the cultivation in similar levels as the control carrying only the output plasmid (FIGS. 2A to 2C).

Testing System Versatility

Figure 3A:
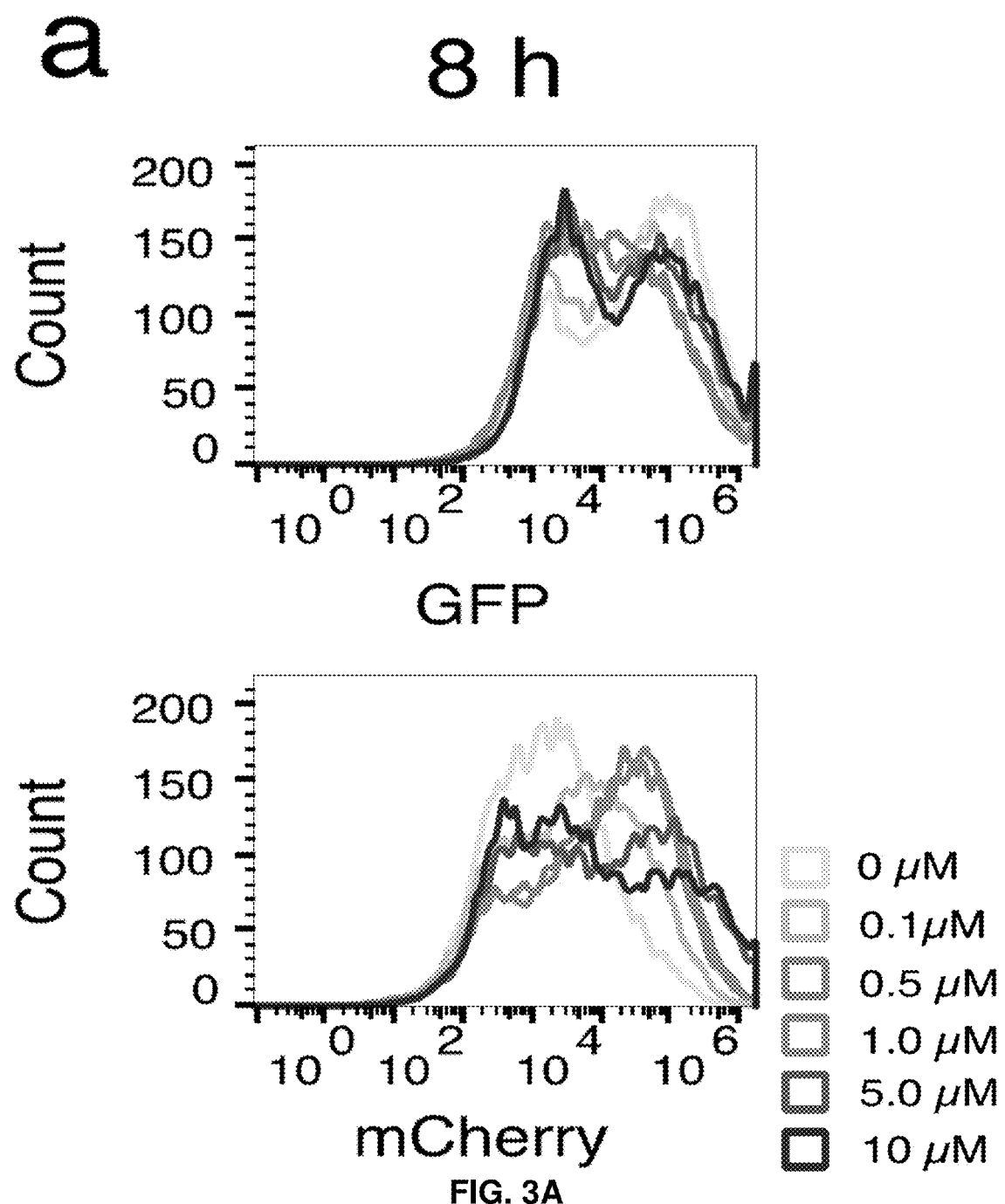
FIG. 3A shows histograms of GFP and mCherry expression in various α-factor concentrations and with various promoters controlling the output. GFP and mCherry production after 8 h in a range from low to high (bright blue to dark blue) concentration of α-factor. The histograms are a representative sample out of three or more biological replicates.
Figure 3B:
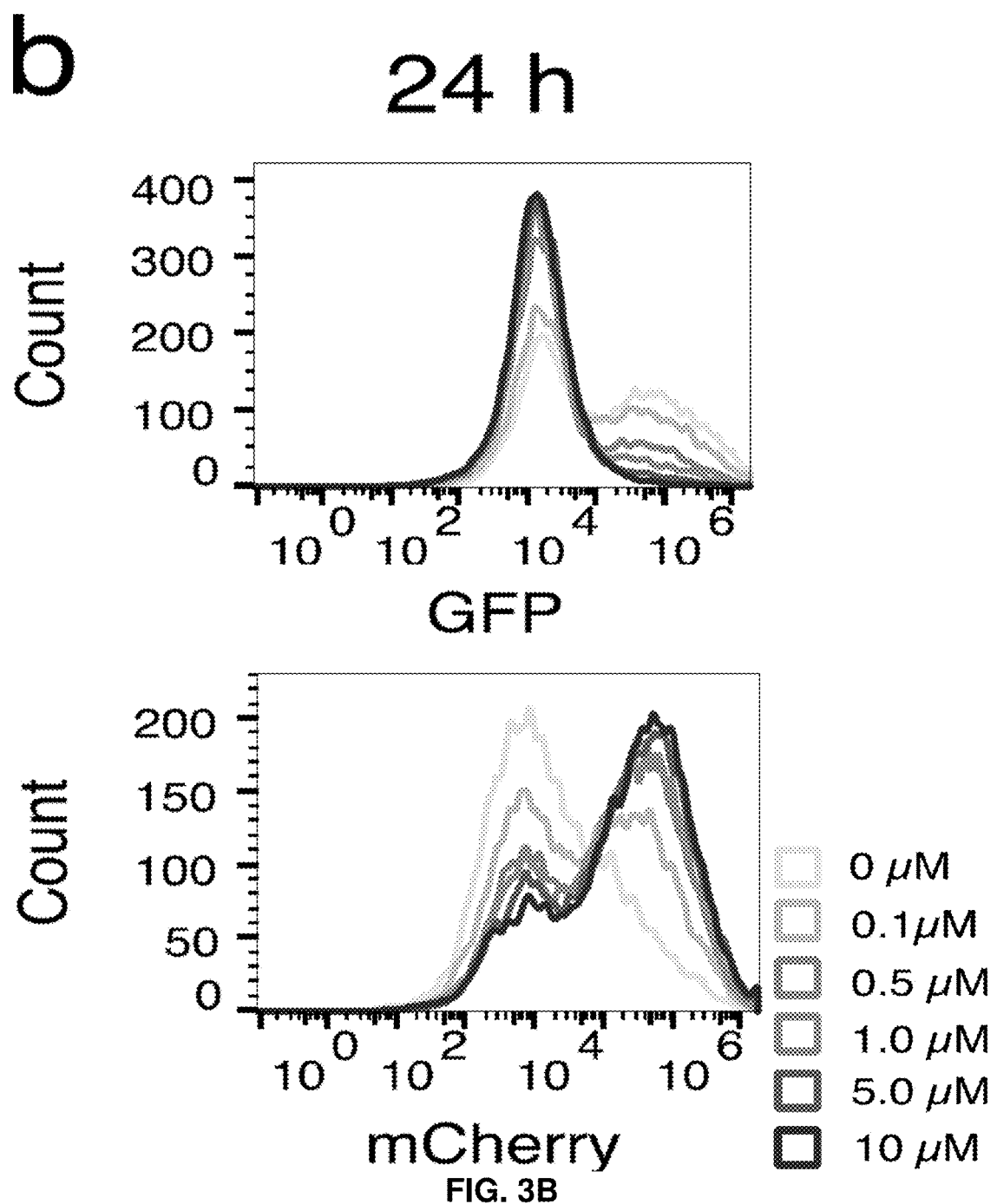
FIG. 3B shows histograms of GFP and mCherry expression in various α-factor concentrations and with various promoters controlling the output. GFP and mCherry production after 24 h in a range from low to high (bright blue to dark blue) concentration of α-factor. The histograms are a representative sample out of three or more biological replicates.

To test the system titratability and tunability, the effect of varying α-factor concentration and using different promoters to control GFP and mCherry expression on the output plasmid is investigated. First, JL275 is transformed with pFUS1J2-ubiM-Cre together with pTEF1-loxP-GFP-loxP-mCherry. The strain is as described above, however, the system is induced by addition of 0, 0.1, 0.5, 1, 5 or 10 μM α-factor. Results showed that the system is titratable, with mCherry output correlating to the amount of α-factor added to the medium (FIGS. 3A and 3B).

To test system tunability, the TEF1 promoter on the output plasmid is replaced by four different native yeast promoters of different strengths; pTDH3, pHHF2, pHSP26 and pHXT7, resulting in plasmids pTDH3-, pHHF2-, pHSP26-, and pHXT7-loxP-GFP-loxP-mCherry. Those plasmids are to be transformed to JL275 together with input plasmid pFUS1J2-ubiM-Cre and tested according to the previously established strain characterization protocol.

Engineering a Control Module

To establish an autoinducible expression system, the α-factor-expressing gene MFα1 needs to be integrated into the genome so that α-factor can be produced endogenously by the cells. However, without a control mechanism, this would lead to premature induction of production. To solve this, a gene encoding the α-factor degrading protease Bar1 is introduced into the input plasmid under control of a doxycycline-inducible promoter, resulting in plasmid pFUS1J2-ubiM-Cre pTDH3-rtTA pTETO3-BAR1.

Figure 4A:
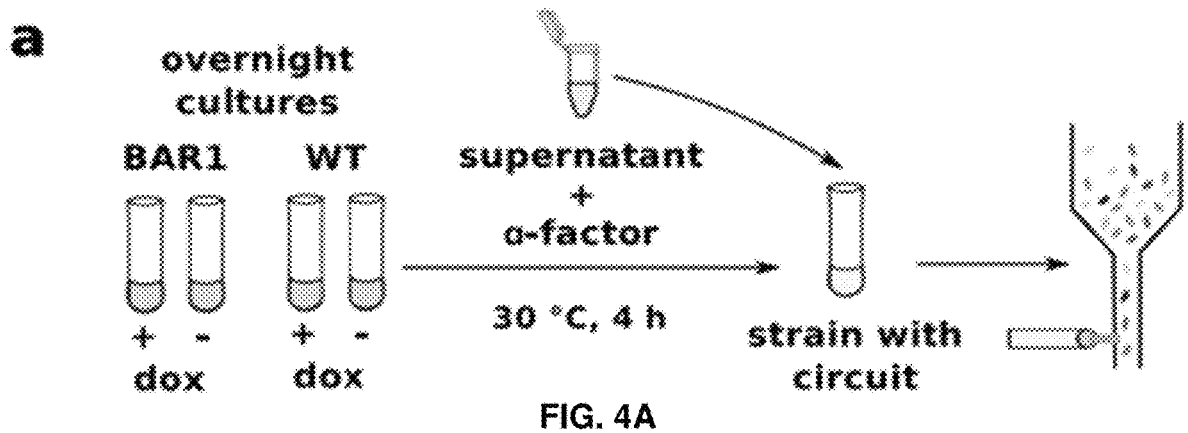
FIG. 4A shows an experimental scheme for testing the functionality of inducible BAR1 expression.
Figure 4B:
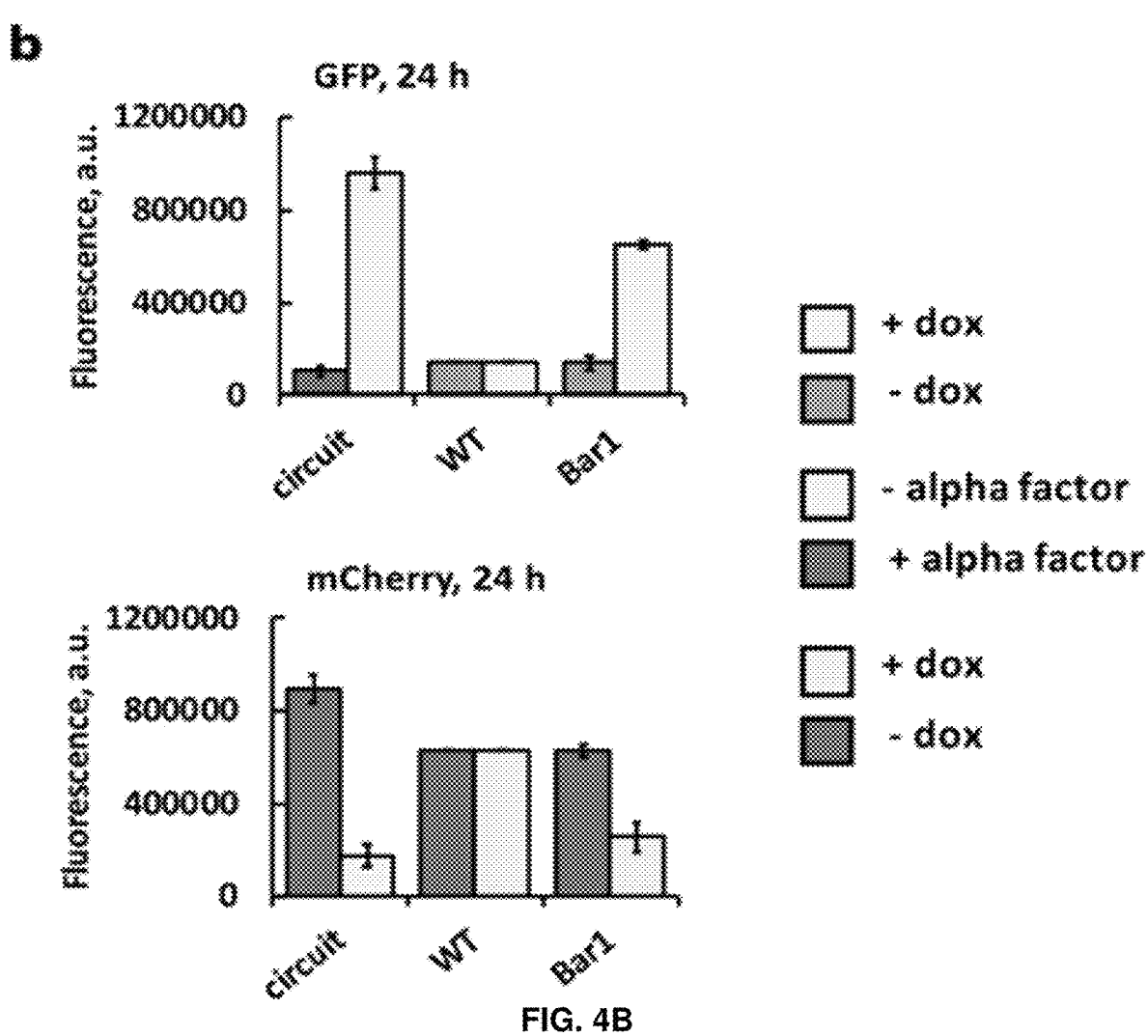
FIG. 4B shows GFP (upper panel) and mCherry (lower panel) production in strain JL275 with pFUS1J2-ubiM-Cre and pTEF1-loxP-GFP-loxP-mCherry after 24 h. The strain was induced with a supernatant/α-factor mix from strain JL275 with pFUS1J2-ubiM-Cre pTDH3-rtTA pTETO3-BAR1 or control plasmid pFUS1-Cre that had been grown to stationary phase with or without doxycycline. The bar graphs represent an average from three biological replicates. Standard deviation is shown as error bars.

The functionality of Bar1 expression is investigated by transforming JL275 with pFUS1J2-ubiM-Cre pTDH3-rtTA pTETO3-BAR1 or control plasmid pFUS1-Cre. Both strains are inoculated in media with or without 5 μg/mL doxycycline, and are grown to stationary phase where after they are spun down. 0.5 mL supernatant is mixed with 0.5 mL 600 μM α-factor and incubated at 30° C. for 4 h. A corresponding amount of 5 μM α-factor (assuming no α-factor has been degraded) from each supernatant/α-factor incubation mix is used to induce cultures of JL275 with pFUS1J2-ubiM-Cre and pTEF1-loxP-GFP-loxP-mCherry (FIG. 4A). 0 and 5 μM α-factor are used as controls. Results showed that the Bar1 plasmid is indeed functional, as JL275 with pFUS1J2-ubiM-Cre and pTEF1-loxP-GFP-loxP-mCherry induced with the supernatant from JL275 with pFUS1J2-ubiM-Cre pTDH3-rtTA pTETO3-BAR1 grown in doxycycline display a similar production pattern as the control where no α-factor is added, indicating that addition of doxycycline induces Bar1 production, and that the Bar1 present in the supernatant is functional and degrades α-factor (FIG. 4B).

Establishing Autoinducible Strains

Figure 5:
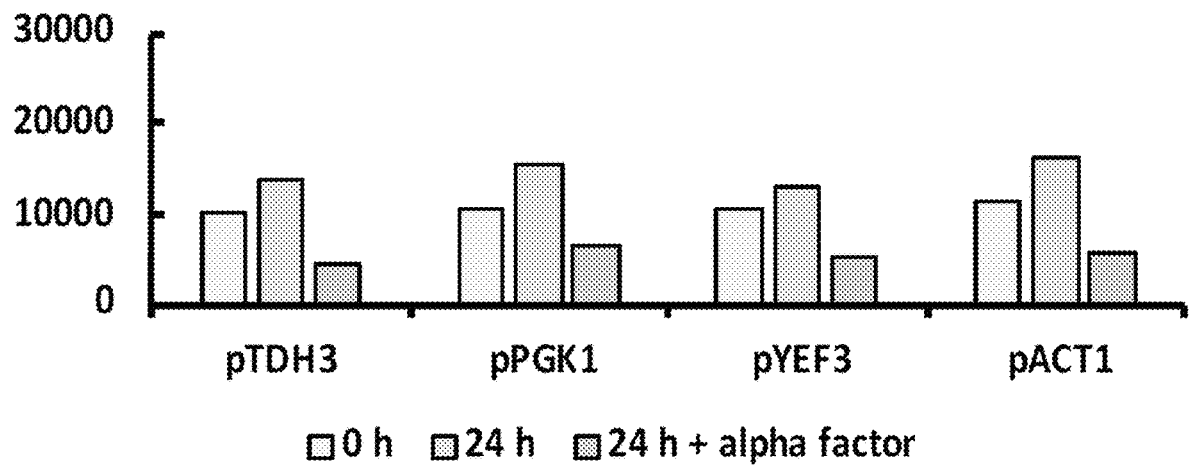
FIG. 5 shows production of GFP and mCherry at 0 and 24 h, with or without addition of α-factor, in strains JL277-280 (pTDH3-pACT1) harboring pFUS1J2-ubiM-Cre pTDH3-rtTA pTETO3-BAR1 and pTEF1-loxP-GFP-loxP-mCherry.
Figure 5:
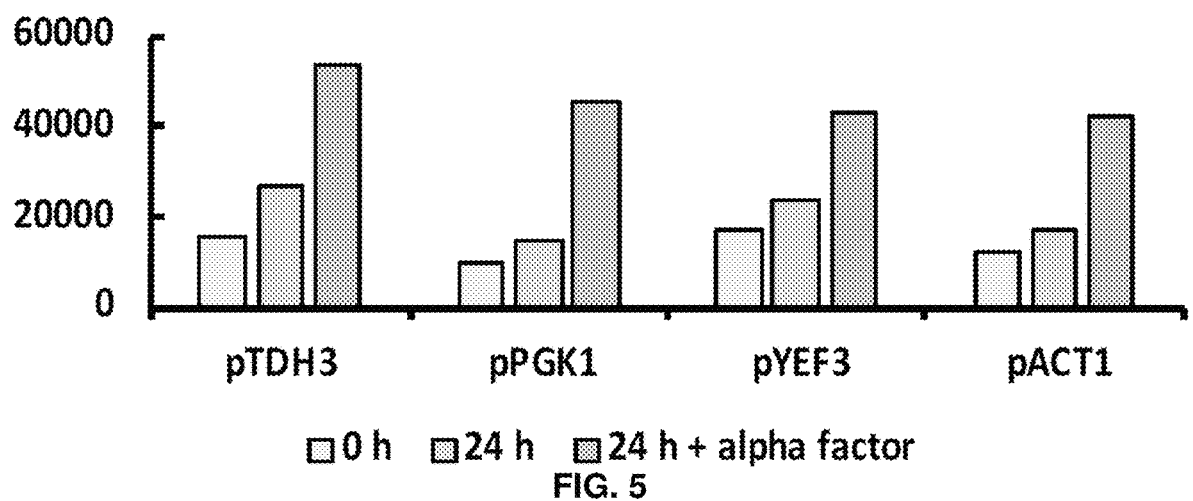

To establish autoinducible strains, the α-factor-expressing gene MFα1 under control of four different native promoters with different expression strengths (pTDH3, pPGK1, pYEF3 and pACT1) is integrated into locus p416d into the genome of JL275, resulting in strains JL277-JL280, respectively. The strains are transformed with plasmids pFUS1J2-ubiM-Cre pTDH3-rtTA pTETO3-BAR1 and pTEF1-loxP-GFP-loxP-mCherry, inoculated into CSM-ura-leu supplemented with 5 μg/mL doxycycline and pre-cultured for two days. The pre-cultures are washed and inoculated to an OD of 0.05, and grown with or without 5 μM α-factor to compare endogenous and external inducibility. The strain fluorescence is measured with a TECAN plate reader. Results showed that mCherry production in strains JL277-280 is barely induced unless α-factor is added to the media (FIG. 5). The strain also continued to produce GFP unless α-factor is added. This experiment is to be repeated according to the previously established strain characterization protocol and measured with a flow cytometer.

Autoinducible System Optimization

Since there is little to no induction of the system in the strains with endogenous α-factor production, two different engineering approaches are taken to improve the α-factor production strength and sensing.

In the first approach, the native gene encoding the Ste2 receptor is knocked out from JL275, resulting in strain JL276. Thereafter, the STE2 gene is integrated into locus 1021b of JL276 under control of four different native promoters with different expression strengths (pTDH3, pPGK1, pYEF3 and pACT1), resulting in strains JL280-284, respectively. Thereafter, MFα1 under control of four different native promoters with different expression strengths (pTDH3, pPGK1, pYEF3 and pACT1) is integrated into locus p416d in strains JL280-284, resulting in strains JL286-301 (see Table 2 for a strain list with phenotype of each strain). These strains are to be transformed with pFUS1J2-ubiM-Cre pTDH3-rtTA pTETO3-BAR1 and with pTEF1-loxP-GFP-loxP-mCherry and tested according to the previously established strain characterization protocol. They will also be tested with the new input plasmids described below. It is expected that the variation of MFα1 and STE2 expression leads to improved responsiveness of the system.

In the second approach, the input plasmid is engineered by addition of a positive feedback loop. Two versions of the input plasmid have been constructed by additions to the pFUS1J2-ubiM-Cre pTDH3-rtTA pTETO3-BAR1. The first version harbors the MFα1 gene under control of pFUS1J2, and the second version harbors the MFα1 gene under control of pTDH3. These plasmids are to be transformed into JL277-JL280 and JL286-301 together with pTEF1-loxP-GFP-loxP-mCherry and be tested according to the previously established strain characterization protocol. It is expected that the increased production of MFα1 from the positive leads to improved responsiveness of the system.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A system comprising: (a) a first nucleic acid encoding an α-factor receptor operatively linked to a first promoter, (b) a second nucleic acid encoding a recombinase operatively linked to a promoter which is activated by the α-factor receptor bound to a yeast α-factor, and (c) a third nucleic acid comprising a gene of interest (GOI) flanked by a pair of recombinase recognition sequences, recognized by the recombinase, operatively linked to a second promoter; wherein the yeast α-factor is MFα1 gene product and the α-factor receptor is STE2, and the recombinase is one selected from the following:

| # | Name | Host |
| --- | --- | --- |
| 1 | BSu_xerC | Bacillus subtilis |
| 2 | BSu_xerD | Bacillus subtilis |
| 3 | BSu_ydcL | Bacillus subtilis |
| 4 | CBu_tnpA | Clostridium butyricum |
| 5 | Col1D | Escherichia coli |
| 6 | CP4-57 | Escherichia coli |
| 7 | Cre | Escherichia coli |
| 8 | D29 | Mycobacterium smegmatis |
| 9 | DLP12 | Escherichia coli |
| 10 | DNo_int | Dichelobacter nodosus |
| 11 | ECo_fimB | Escherichia coli |
| 12 | ECo_fimE | Escherichia coli |
| 13 | ECo_orf | Escherichia coli |
| 14 | ECo_xerC | Escherichia coli |
| 15 | ECo_xerD | Escherichia coli |
| 16 | HIn_orf | Haemophilus influenzae |
| 17 | HIn_rci | Haemophilus influenzae |
| 18 | HIn_xerC | Haemophilus influenzae |
| 19 | HIn_xerD | Haemophilus influenzae |
| 20 | HK22 | Escherichia coli |
| 21 | HP1 | Haemophilus influenzae |
| 22 | L2 | Acholeplasma sp. |
| 23 | L5 | Mycobacterium tuberculosis |
| 24 | L54 | Staphylococcus aureus |
| 25 | Lambda | Escherichia coli |
| 26 | LLe_orf | Lactobacillus leichmannii |
| 27 | LLe_xerC | Lactobacillus leichmannii |
| 28 | phi10MC | Oenococcus oeni |
| 29 | MJa_orf | Methanococcus jannaschi |
| 30 | MLe_xerD | Mycobacterium leprae |
| 31 | MPa_int | Mycobacterium paratuberculosis |
| 32 | MTu_int | Mycobacterium tuberculosis |
| 33 | MTu_xerC | Mycobacterium tuberculosis |
| 34 | MV4 | Lactobacillus delbrueckii |
| 35 | MX8 | Myxococcus xanthus |
| 36 | pAE1 | Alcaligenes eutrophus |
| 37 | pCL1 | Chlorobium limicola |
| 38 | pDU1 | Nostoc sp. |
| 39 | pMEA | Amycolatopsis methanolica |
| 40 | RSp_EF | Rhizobium sp. |
| 41 | RSp_GC | Rhizobium sp. |
| 42 | RSp_QK | Rhizobium sp. |
| 43 | RSp_RA | Rhizobium sp. |
| 44 | RSp_RB | Rhizobium sp. |
| 45 | RSp_RC | Rhizobium sp. |
| 46 | RSp_RD | Rhizobium sp. |
| 47 | RSp_RE | Rhizobium sp. |
| 48 | RSp_RF | Rhizobium sp. |
| 49 | pSAM2 | Streptomyces ambofaciens |
| 50 | pSDL2 | Salmonella dublin |
| 51 | pSE101 | Saccharopolyspora erythraea |
| 52 | pSE211 | Saccharopolyspora erythraea |
| 53 | pWS58 | Lactobacillus delbrueckii |
| 54 | phi-11 | Staphylococcus aureus |
| 55 | phi-13 | Staphylococcus aureus |
| 56 | phi-80 | Escherichia coli phage |
| 57 | phi-adh | Lactobacillus gasseri |
| 58 | phi-CTX | Pseudomonas aeruginosa |
| 59 | phi-g1e | Lactobacillus sp. |
| 60 | phi-LC3 | Lactococcus lactis |
| 61 | phi-R73 | Escherichia coli |
| 62 | P186 | Escherichia coli |
| 63 | P2 | Escherichia coli |
| 64 | P21 | Escherichia coli |
| 65 | P22 | Salmonella typhimurium |
| 66 | P4 | Escherichia coli |
| 67 | P434 | Escherichia coli |
| 68 | PAe_xerC | Pseudomonas aeruginosa |
| 69 | PMi_fimB | Proteus mirabilis |
| 70 | R721 | Escherichia coli |
| 71 | Rci | Escherichia coli |
| 72 | SF6 | Shigella flexneri |
| 73 | SLP1 | Streptomyces coelicolor |
| 74 | IntI3 | Serratia marcescens |
| 75 | SsrA | Methanosarcina acetivorans |
| 76 | SSV1 | Sulfolobus sp. |
| 77 | T12 | Streptococcus pyogenes |
| 78 | IntI1 | Escherichia coli |
| 79 | Tn4430 | Bacillus thuringiensis |
| 80 | Tn5041 | Pseudomonas sp. |
| 81 | Tn5252 | Streptococcus pneumoniae |
| 82 | Tn5276 | Lactobacillus lactis |
| 83 | Tn554a | Staphylococcus aureus |
| 84 | Tn554b | Staphylococcus aureus |
| 85 | IntI2 | Escherichia coli |
| 86 | Tn916 | Entercoccus faecalis |
| 87 | Tuc | Lactobacillus lactis |
| 88 | BZo_int | Bergeyella zoohelcum |
| 89 | ASp_xisA | Anabaena sp. |
| 90 | ASp_xisC | Anabaena sp. |
| 91 | FLP | Saccharomyces cerevisiae |
| 92 | pKD1 | Kluyveromyces lactis |
| 93 | pSB2 | Zygosaccharomyces bailii |
| 94 | pSB3 | Zygosaccharomyces bisporus |
| 95 | pSM1 | Zygosaccharomyces fermentati |
| 96 | pSR1 | Zygosaccharomyces rouxii |
| 97 | HPy_xerC | Helicobacter pylori |
| 98 | HPy_xerD | Helicobacter pylori |

-continued

| # | Name | Host |
|---|---|---|
| 99 | Eco_Rac | *Escherichia coli* |
| 100 | Eco_Qin | *Escherichia coli* |
| 101 | CP4-6 | *Escherichia coli* |
| 102 | E14 | *Escherichia coli.* |

2. The system of claim 1, wherein the first promoter is a native promoter of STE2.

3. The system of claim 1, wherein the promoter which is activated by an α-factor receptor bound to an α-factor is a FUS1 promoter.

4. The system of claim 1, wherein the first nucleic acid is stably integrated in a chromosome.

5. The system of claim 1, wherein the second promoter is a constitutive promoter.

6. The system of claim 1, wherein the second nucleic acid is stably integrated into a chromosome.

7. The system of claim 1, wherein the second nucleic acid is an input plasmid.

8. The system of claim 1, wherein the third nucleic acid is an output plasmid.

9. The system of claim 1, wherein the recombinase is *Escherichia coli* Cre, *Escherichia coli* FimE, *Zygosaccharomyces bailii* pSB2, *Zygosaccharomyces fermentati* pSM1, *Helicobacter pylori* XerC, or *Helicobacter pylori* XerD.

10. The system of claim 1, wherein the recombinase comprises a protein degradation tag.

11. The system of claim 1, wherein the promoter which is activated by an α-factor receptor bound to an α-factor is a FUS1/2 promoter.

12. The system of claim 1, wherein the first promoter is a first inducible promoter.

13. The system of claim 1, wherein the first nucleic acid further comprises a MFα1 gene operatively linked to a second inducible promoter.

14. The system of claim 1, wherein the nucleic acid encoding the x-factor receptor is operatively linked to $P_{STE2}$ and/or $P_{VAR*}$.

15. The system of claim 1, wherein the second nucleic acid further comprises nucleic acid encoding BAR1 operatively linked to $P_{TETO3}$, and/or nucleic acid encoding rtTA* operatively linked to $P_{TDH3}$.

16. A genetically modified fungal cell comprising the system of claim 1, wherein the fungal cell is a yeast cell with an endogenous α-factor.

17. The genetically modified fungal cell of claim 16, wherein the yeast cell is a *Saccharomyces* cell.

18. The genetically modified fungal cell of claim 17, wherein the *Saccharomyces* cell is a *Saccharomyces cerevisiae* cell.

19. The genetically modified fungal cell of claim 18, wherein the *Saccharomyces cerevisiae* cell is a cell of the *Saccharomyces cerevisiae* BY4741 strain.

20. A method comprising: (a) providing a system of claim 1, (b) introducing or expressing an α-factor to the system, and (c) expressing the GOI.

21. A method comprising: (a) providing a genetically modified fungal cell of claim 16, (b) introducing or expressing an α-factor to the system, and (c) expressing the GOI.

* * * * *